(12) United States Patent
Kubo et al.

(10) Patent No.: US 11,313,851 B2
(45) Date of Patent: Apr. 26, 2022

(54) DEVICE, SYSTEM, AND KIT FOR MEASURING TENSION OF CELL STRUCTURE CONTAINING MUSCLE CELLS

(71) Applicant: NIHON KOHDEN CORPORATION, Tokyo (JP)

(72) Inventors: Hirotsugu Kubo, Tokorozawa (JP); Takahiro Shioyama, Tokorozawa (JP); Yuki Kagawa, Tokorozawa (JP); Yuto Hinata, Tokorozawa (JP); Hodaka Makino, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 143 days.

(21) Appl. No.: 16/803,617

(22) Filed: Feb. 27, 2020

(65) Prior Publication Data

US 2020/0278342 A1    Sep. 3, 2020

(30) Foreign Application Priority Data

Feb. 28, 2019  (JP) .............................. JP2019-036677
Feb. 17, 2020  (JP) .............................. JP2020-024512

(51) Int. Cl.
*G01N 33/00*   (2006.01)
*B01L 3/00*    (2006.01)
(Continued)

(52) U.S. Cl.
CPC ......... *G01N 33/5032* (2013.01); *C12M 23/46* (2013.01); *C12M 41/46* (2013.01); *G01N 33/5014* (2013.01)

(58) Field of Classification Search
CPC .............................. C12M 35/00; C12M 35/04
See application file for complete search history.

(56) References Cited

U.S. PATENT DOCUMENTS 5,284,766 A   2/1994  Okano et al.
9,289,454 B2  3/2016  Sekine et al.
(Continued)

FOREIGN PATENT DOCUMENTS

EP  3 477 302 A1  5/2019
JP   2-211865 A    8/1990
(Continued)

OTHER PUBLICATIONS

Communication dated Jan. 30, 2019 issued by the European Patent Office in counterpart European Application No. 18201938.0.
(Continued)

*Primary Examiner* — Nathan A Bowers
(74) *Attorney, Agent, or Firm* — Sughrue Mion, PLLC

(57) ABSTRACT

A device for measuring a tension of a cell structure containing muscle cells includes a first and a second gel adaptor holder. The first gel adaptor holder includes a frame member and a first gel holding portion which is disposed protrudingly from a part of an inner surface of the frame member for fixing one end of a gel. The second gel adaptor holder includes a second gel holding portion that fixes another end of the gel, and connecting members connected with the second gel holding portion. A kit including the device, a substrate and a gel forming cover. The substrate includes a pair of gel shaping convex parts fitted along the inner surface of the frame member. The gel forming cover includes a surface parallel to a gel contacting surface of the substrate, in order to form an upper surface of the gel.

18 Claims, 33 Drawing Sheets

(51) Int. Cl.
   *C12M 3/00* (2006.01)
   *G01N 33/50* (2006.01)
   *C12M 1/34* (2006.01)

(56) References Cited

U.S. PATENT DOCUMENTS

| | | | |
|---|---|---|---|
| 9,617,519 B2 | 4/2017 | Sakaguchi et al. | |
| 2004/0235153 A1* | 11/2004 | Takagi | C12M 35/04 435/293.2 |
| 2007/0178584 A1* | 8/2007 | Naruse | C12M 23/26 435/289.1 |
| 2011/0117645 A1 | 5/2011 | Yasuda et al. | |
| 2012/0219981 A1* | 8/2012 | Muthiah | C12M 35/04 435/29 |
| 2013/0337554 A1* | 12/2013 | Chang | C12M 23/46 435/292.1 |
| 2019/0093063 A1* | 3/2019 | Subramanian | C12Q 1/6883 |
| 2019/0390152 A1* | 12/2019 | Li | C12M 41/48 |

FOREIGN PATENT DOCUMENTS

| | | |
|---|---|---|
| WO | 2009/123349 A1 | 10/2009 |
| WO | 2012/036224 A1 | 3/2012 |
| WO | 2012/036225 A1 | 3/2012 |
| WO | 2015/134589 A1 | 9/2015 |

OTHER PUBLICATIONS

Yuji Haraguchi et al., "Scaffold-free tissue engineering using cell sheet technology", RSC Advances, vol. 2, The Royal Society of Chemistry, 2012, pp. 2184-2190.

Michael R Zile et al., "Gel stretch method: a new method to measure constitutive properties of cardiac muscle cells", AJP—Heart and Circulatory Physiology, XP55545731, Jun. 1, 1998, 16 pages, Retrieved from URL: <https://www.physiology.org/doi/pdf/10.1152/ajpheart.1998.274.6.H2188>.

Zhonggang Feng et al., "An Electro-Tensile Bioreactor for 3-D Culturing of Cardiomyocyte", IEEE Engineering in Medicine and Biology Magazine, IEEE Service Center, Pisacataway, NJ, XP002682110, Jul. 1, 2005, 8 pages.

Daisuke Sasaki et al., "Contractile force measurement of human induced pluripotent stem cell-derived cardiac cell sheet-tissue", PLOS One, vol. 13, No. 5, XP055545535, May 23, 2018, 22 pages.

Yimu Zhao et al., "A Platform for Generation of Chamber-Specific Cardiac Tissues and Disease Modeling", Cell press, vol. 176, Elsevier, Feb. 7, 2019, 34 pages.

Katsuhisa Matsuura et al., "Creation of human cardiac cell sheets using pluripotent stem cells", Biochemical and Biophysical Research Communications, vol. 425, Elsevier, Aug. 24, 2012, pp. 321-327.

* cited by examiner

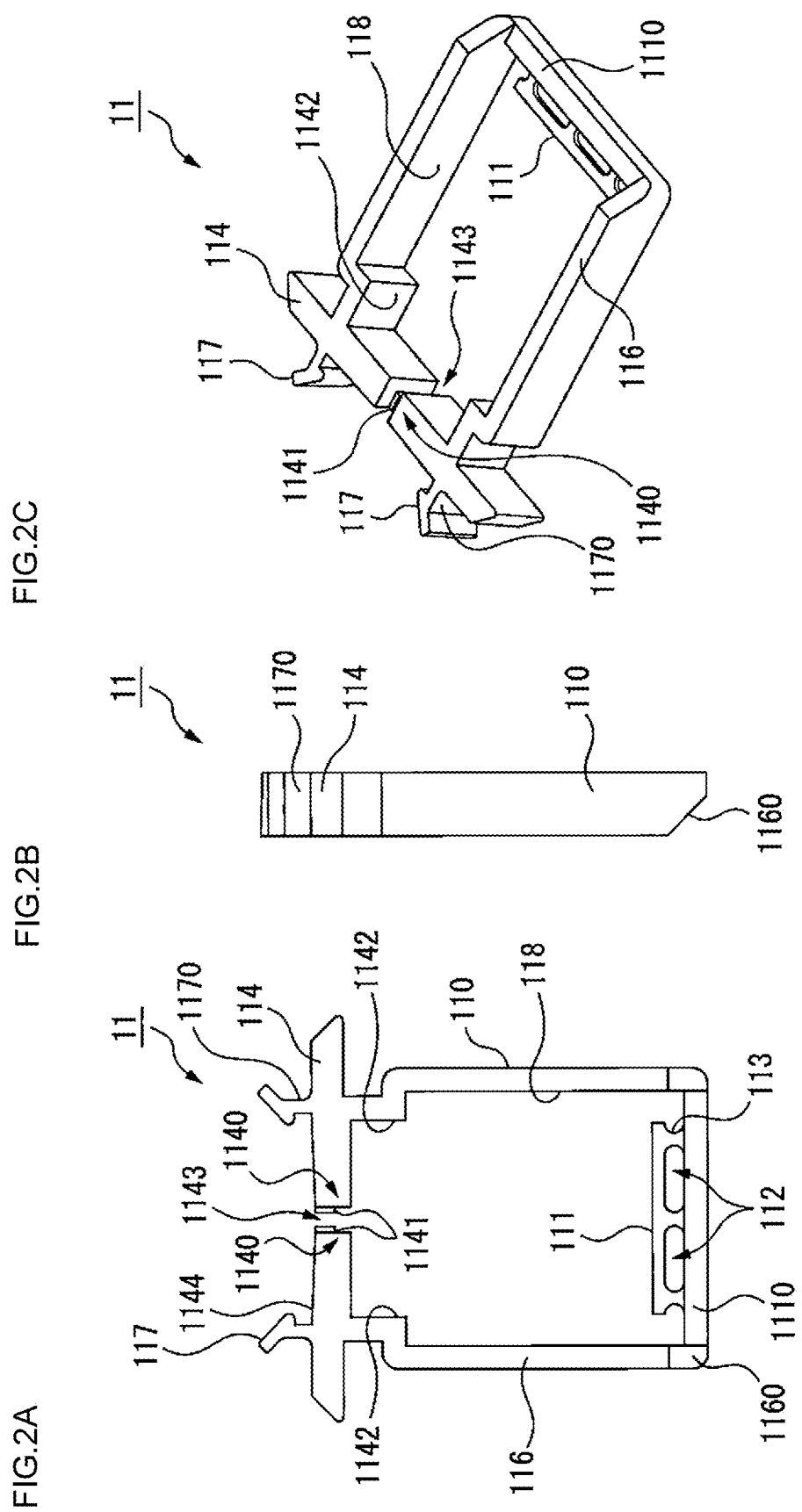

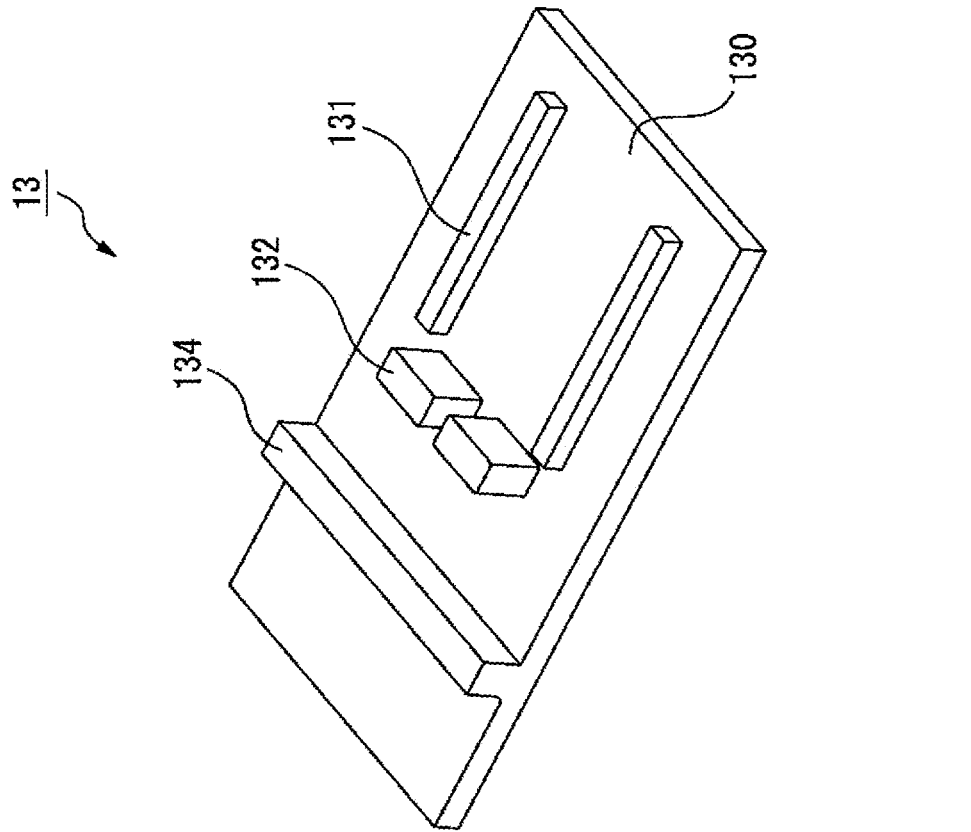
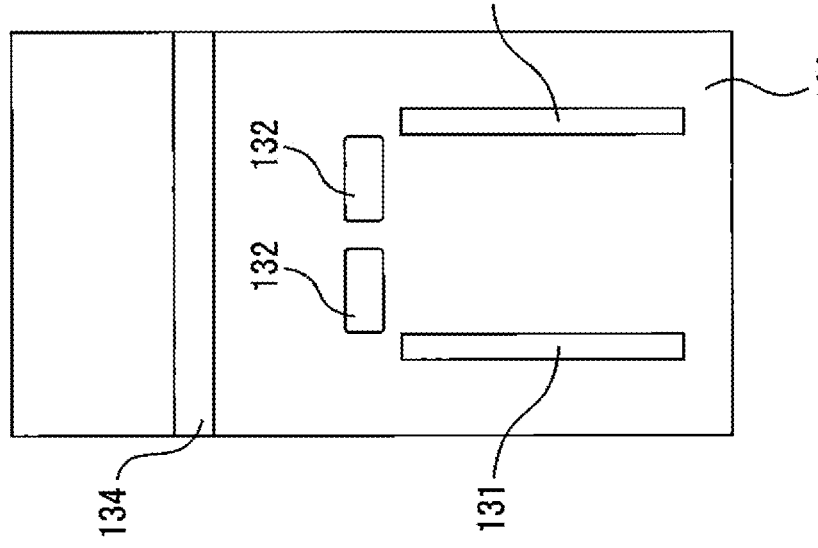

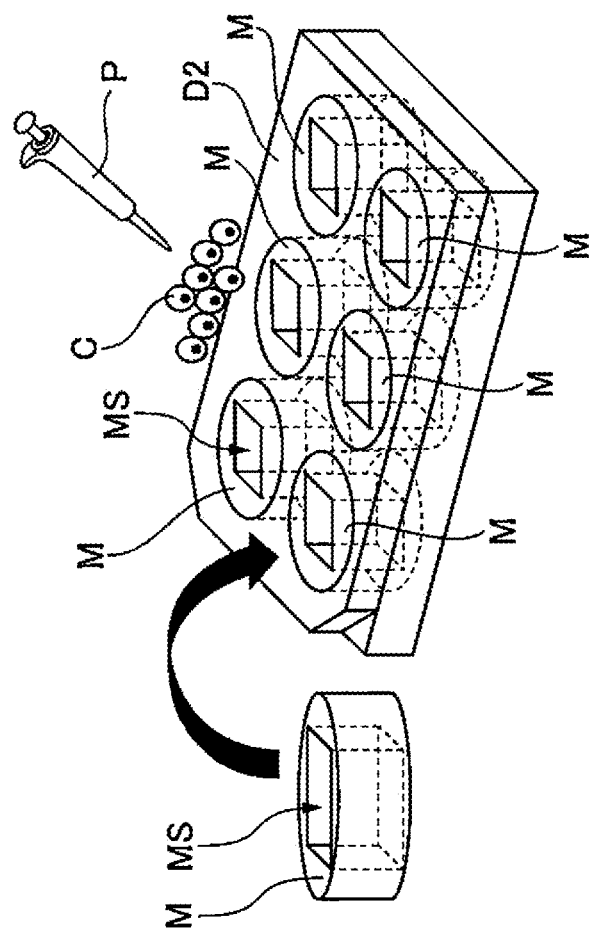
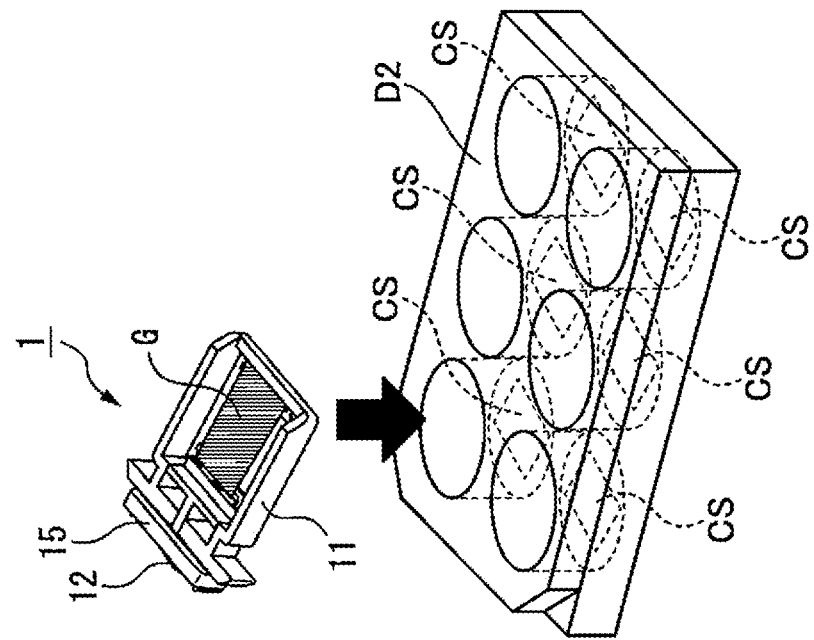

FIG.10A
FIG.10B
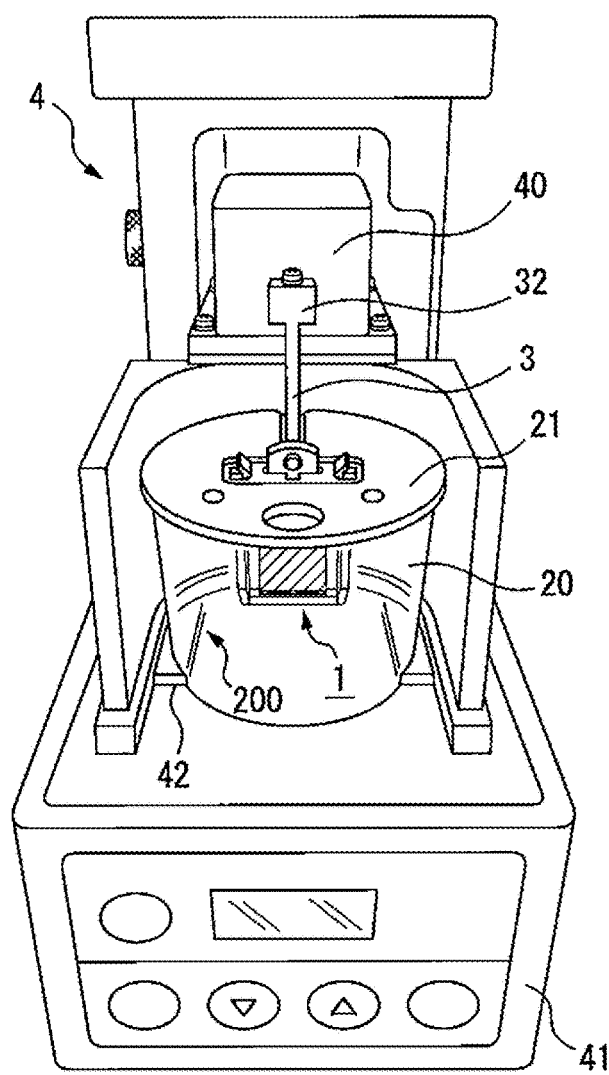
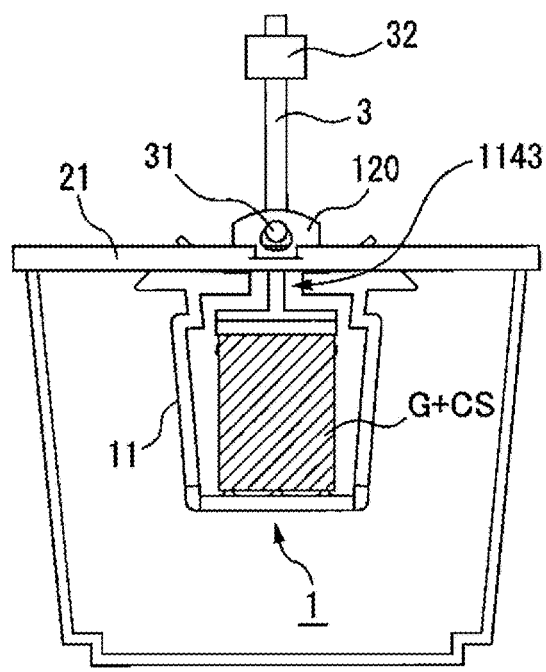

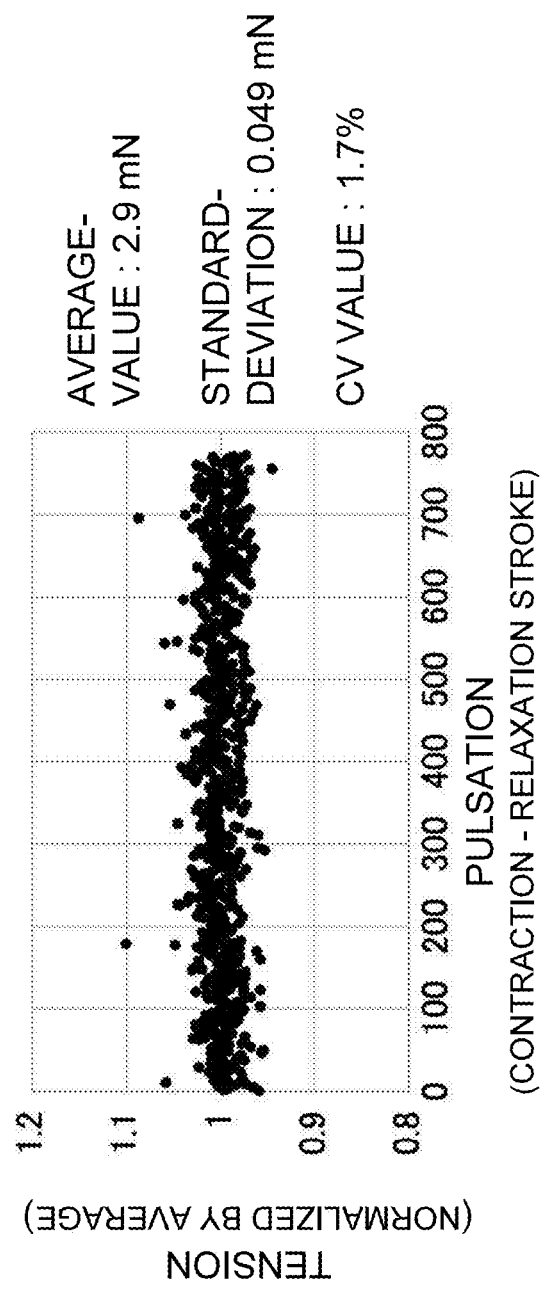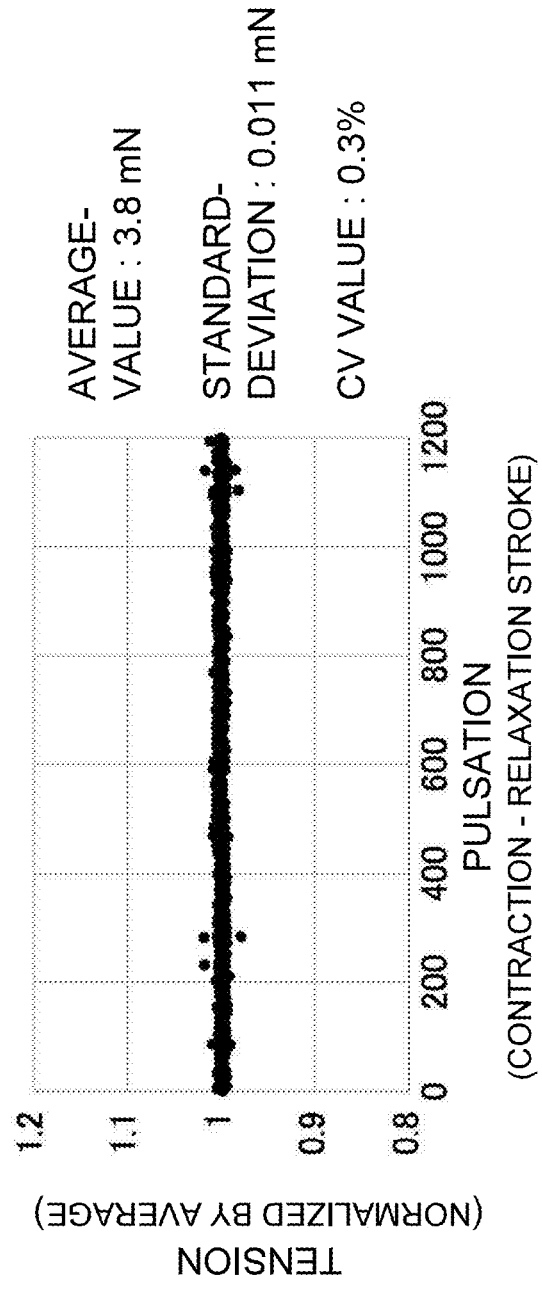

64

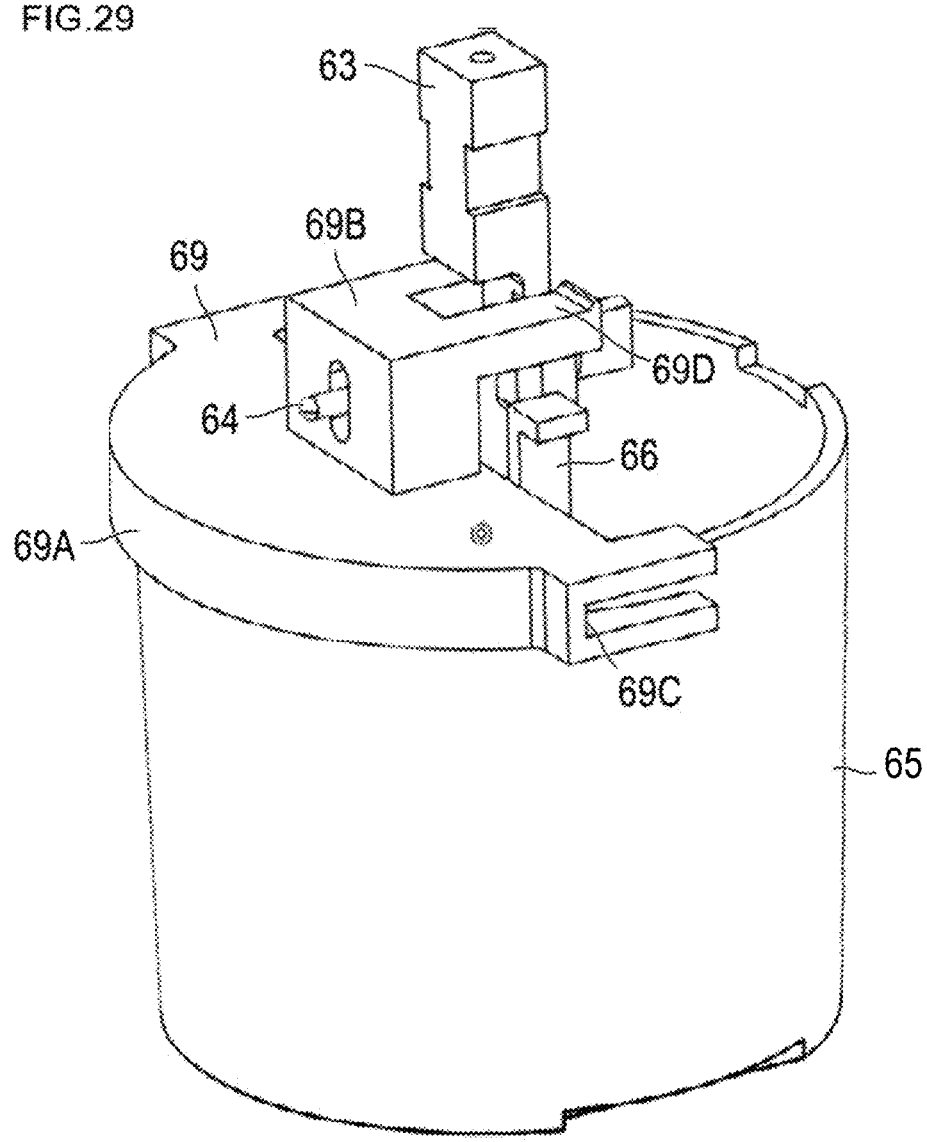
FIG.29
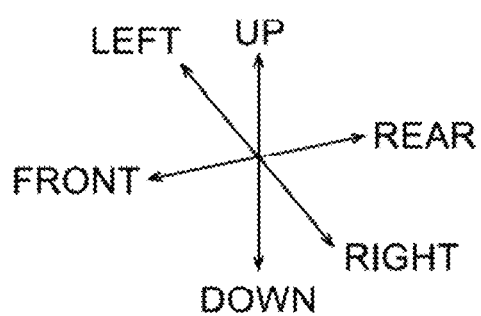

71

DEVICE, SYSTEM, AND KIT FOR MEASURING TENSION OF CELL STRUCTURE CONTAINING MUSCLE CELLS

CROSS-REFERENCE TO RELATED APPLICATION

This application claims priority from Japanese Patent Applications No. 2019-036677, filed on Feb. 28, 2019, and No. 2020-024512, filed on Feb. 17, 2020, the entire subject matter of them are incorporated herein by reference.

TECHNICAL FIELD

The presently disclosed subject matter relates to a device, system, and kit for measuring the tension of a cell structure containing muscle cells.

BACKGROUND

In drug discovery research, an in vitro test using cultured cells, and a in vivo test using experimental animals are conducted in order to evaluate the safety and effectiveness of the developed drug. In the former, an in vitro culture system of animal cells is used. In the latter, an evaluation is performed by a system using experimental animals such as rodents.

It is usually said that the success rate of drug discovery is about one six-thousandth. Because of numerous failures of development of candidate drugs, the research development cost in a drug company or the like tends to be increased. Usually, it is said that investment of several ten billion yen is required to develop one kind of new drug. A failure of development of new drug is considered to be mainly caused by (1) the difference between an evaluation screening system using cells alone, and actual living body tissue of a human, and (2) the difference between an experimental animal and a human. In a site of new drug development. it is requested to eliminate these differences, to improve the success rate of drug discovery, and to reduce the research development cost.

Recently, a drug discovery screening method that uses pluripotent stem cells such as iPS cells having the ability to differentiate into various functional cells has been developed. In a conventional evaluation system, however, cells alone are used, and the condition of living body tissue is not reflected. Therefore, it is requested to develop an evaluation system that imitates living body tissue from somatic cells which are differentiated from pluripotent stem cells.

As an attempt to construct three-dimensional tissues by using single cells, the following methods, for example, have been developed; a method in which cells are seeded to a three-dimensional structure that is called a scaffold, that in which organs or tissues are decellularized, and cells are seeded to the remaining matrix to produce a three-dimensional structure, and that in which cell sheets that are harvested as a sheet-like cell structure are stacked three-dimensionally (for example, JPH02-211865 and Haraguchi Y., et al., Scaffold-free tissue engineering using cell sheet technology. RSC Adv., 2012; 2: 2184-2190).

As one of methods for preparing cell sheets, known is a method in which a cell culture dish (temperature-responsive culture dish) that is coated with poly(N-isopropylacrylamide) (PIPAAm) is used (JPH02-211865). After an arbitrary cells are cultured on a temperature-responsive culture dish coated with PIPAAm, and the cells become confluent, the temperature is set to 20° C. that is lower than 32° C. which is the lower critical solution temperature (LCST) of PIPAAm, and then sheet-like cells (a cell sheet) is non-invasively obtained.

While using such techniques, an evaluation system that is to be used in drug discovery screening is researched and developed. As one of such evaluation systems, an attempt to construct myocardial tissue for evaluating the cardiac toxicity of a candidate drug is performed (for example, WO/2012/036224 and WO/2012/036225). However, construction of an evaluation system by these methods is very cumbersome, and unsuitable for mass production. Moreover, the methods cannot quantitatively measure muscle contraction.

It is requested to develop a novel evaluation system that can be used in a drug discovery screening system, particularly in a cardiac toxicity screening test, that can be mass-produced, and that can be used in simple procedures.

SUMMARY

It is an object of the presently disclosed subject matter to provide a device, system, and kit for measuring the tension of a cell structure containing muscle cells, that can quantitatively measure muscle contraction, and that can be mass-produced.

In order to solve the problem, the inventors conduct researches and developments while studying from various angles, and, as a result, have developed a device, system, and kit for measuring the tension of a cell structure containing muscle cells in which, by improving the form of the device for measuring the tension of a cell structure containing muscle cells, muscle contraction is allowed to be quantitatively measured, and which can be mass-produced. Namely, the presently disclosed subject matter is configured in the following manner. Hereinafter, a device for measuring a tension is often referred to as a tension measuring device, and a system for measuring a tension is often referred to as a tension measuring system.

[1] A device for measuring a tension of a cell structure containing muscle cells, wherein the device includes:

a first gel adaptor holder that includes: a frame member; and a first gel holding portion that, for fixing one end of a gel, is disposed protrudingly from a part of a side inner surface of the frame member, the frame member including: a cutaway in an upper portion of the frame member at a position opposed to the first gel holding portion; and a pair of first grasping portions that are formed by the cutaway, an upper portion of the frame member having a pair of claw portions; and a second gel adaptor holder that includes: a second gel holding portion for fixing another end of the gel; and a connecting portion that is connected to the second gel holding portion through a coupling portion.

The second gel adaptor holder is attached to the first gel adaptor holder by causing the first grasping portions to grasp the connecting portion so that, inside the frame member, the second gel holding portion is opposed to the first gel holding portion.

A gap between the pair of first grasping portions is increased when the pair of claw portions are fitted to a cover of a culture medium tank.

[2] The device according to [1] wherein the muscle cells are at least one selected from a group consisting of myocardial cells, skeletal muscle cells, and smooth muscle cells.

[3] The device according to [1] or [2] wherein the cell structure includes a shape that is at least one selected from a group consisting of a sheet-like shape, a rod-like shape, and a string-like shape.

[4] The device according to any one of [1] to [3] wherein the first gel holding portion includes one or more first gel holding ports, and the second gel holding portion includes one or more second gel holding ports.

[5] The device according to [4] wherein two to five each of the first gel holding ports and the second gel holding ports are disposed.

[6] The device according to any one of [1] to [5] wherein the first gel holding portion and the second gel holding portion are thinner than the frame member.

[7] The device according to any one of [1] to [6] wherein the frame member has a thickness of 0.5 mm to 3.0 mm.

[8] The device according to any one of [1] to [7] wherein each of the first grasping portions includes a convex part that is protruded in a direction of grasping the coupling portion, and the coupling portion includes concave parts into which the convex parts are to be fitted, respectively.

[9] The device according to any one of [1] to [8] wherein the frame member includes a second grasping portion for grasping the second gel adaptor holder.

[10] The device according to any one of [1] to [9] wherein a gel is disposed between the first gel holding portion and the second gel holding portion.

[11] The device according to [10] wherein the gel is a hydrogel.

[12] The device according to [10] or [11] wherein the gel is fibrin gel.

[13] The device according to any one of [10] to [12] wherein the device further includes a cell structure containing muscle cells bonded to the gel.

[14] The device according to [13] wherein the muscle cells are at least one selected from a group consisting of myocardial cells, skeletal muscle cells, and smooth muscle cells.

[15] The device according to [13] or [14] wherein the cell structure has a shape that is at least one selected from a group consisting of a sheet-like shape, a rod-like shape, and a string-like shape.

[16] The device according to any one of [13] to [15] wherein the cell structure is a cell sheet.

[17] A system for measuring a tension of a cell structure containing muscle cells, wherein the system includes:
the device according to any one of [13] to [15];
a body of the culture medium tank in which the device is to be immersed;
a culture medium tank cover that includes fitting portions which are to be fitted to the pair of claw portions, and a connecting portion through port through which the connecting portion of the second gel adaptor holder is to be passed, and that covers the culture medium tank body;
a tension detecting unit that is connected to the connecting portion of the second gel adaptor holder;
a calculator that is connected to the tension detecting unit, and that applies a calculation to a signal detected by the tension detecting unit to calculate a tension; and an outputting unit that displays a result of the calculation performed by the calculator.

[18] The system according to [17] wherein the tension detecting unit is a load cell.

[19] A kit for producing the device according to any one of [1] to [15], wherein the kit includes:
a first gel adaptor holder that includes: a frame member; and a first gel holding portion that, for fixing one end of a gel, is disposed protrudingly from a part of a side inner surface of the frame member, the frame member having: a cutaway in an upper portion of the frame member at a position opposed to the first gel holding portion; and a pair of first grasping portions that are formed by the cutaway, an upper portion of the frame member having a pair of claw portions;
a second gel adaptor holder that includes: a second gel holding portion for fixing another end of the gel; and a connecting portion that is connected to the second gel holding portion through a coupling portion;
a substrate that includes a pair of gel shaping convex parts which are fitted along the side inner surface of the frame member; and
a gel forming cover that includes a surface which is parallel to a gel contacting surface of the substrate, in order to form an upper surface of the gel,
the second gel adaptor holder is attached to the first gel adaptor holder by causing the first grasping portions to grasp the connecting portion so that, inside the frame member, the second gel holding portion is opposed to the first gel holding portion, and
a gap between the pair of first grasping portions is increased when the pair of claw portions are fitted to the culture medium tank cover.

[20] The kit according to [19] wherein the first gel holding portion includes one or more first gel holding ports, and the second gel holding portion includes one or more second gel holding ports.

[21] The kit according to [19] or [20] wherein the first gel holding portion and the second gel holding portion are thinner than the frame member.

[22] The kit according to any one of [19] to [21] wherein the kit further includes a gelling agent for producing the gel.

[23] A device for measuring a tension of a cell structure containing muscle cells including:
a first gel adaptor holder including a first gel holding portion for fixing one end of a gel;
a second gel adaptor holder including a second gel holding portion that fixes another end of the gel, and that is disposed to be opposed to the first gel holding portion; and
a fixing portion to which connecting members for connecting the first gel adaptor holder and the second gel adaptor holder to each other are able to be fixed.

[24] The device according to [23],
wherein the first gel adaptor holder includes a first fitting portion, and
wherein the device further includes a culture medium tank in which the first gel adaptor holder and the second gel adaptor holder are accommodated, and which includes a second fitting portion that is configured to be able to be fitted to the first fitting portion.

[25] The device according to [23] or [24] wherein the fixing portion is disposed in the first gel adaptor holder, and able to be engaged with the connecting members.

[26] The device according to any one of [23] to [25] further including a rod that connects a tension detecting unit and the second gel adaptor holder to each other,
wherein the second gel adaptor holder further includes a first elongated portion that is disposed above the second gel holding portion and the cross section is configured like a bullet,
wherein the rod includes a recess portion into which the first elongated portion is to be inserted, and
wherein the second gel adaptor holder and the rod are connected to each other by, in a state where the first elongated portion is inserted into the recess portion, inserting a fixing member into the first elongated portion and the recess portion.

[27] The device according to any one of [23] to [26] wherein the second gel adaptor holder includes a pair of sleeve portions that are slidably inserted into the connecting members, respectively.

[28] A kit for a tension measuring device for measuring a tension of a cell structure containing muscle cells, comprising:

a first gel adaptor holder including a first gel holding portion for fixing one end of a gel;

a second gel adaptor holder including a second gel holding portion that fixes another end of the gel, and that is disposed to be opposed to the first gel holding portion;

connecting members for connecting the first gel adaptor holder and the second gel adaptor holder to each other;

a substrate into which the first gel adaptor holder and the second gel adaptor holder that are connected to each other by the connecting members are to be fitted; and a fixing portion to which the connecting members are able to be fixed.

[29] The kit according to [28], wherein the first gel adaptor holder includes a first fitting portion, and wherein the kit further includes a culture medium tank in which the first gel adaptor holder and the second gel adaptor holder are accommodated, and which includes a second fitting portion that is configured to be able to be fitted to the first fitting portion.

[30] The kit according to [28] or [29] further comprising:

a rod that connects a tension detecting unit and the second gel adaptor holder to each other; and a rod holding jig that is able to be fixed to a top portion of the culture medium tank, and that includes a rod grasping portion which is able to grasp the rod.

According to the presently disclosed subject matter, the tension of a cell structure containing muscle cells can be simply measured. The device of the presently disclosed subject matter can be easily incorporated into a system for measuring the tension of a cell structure containing muscle cells, and enables data to be acquired with high reproducibility and stability.

BRIEF DESCRIPTION OF DRAWINGS

FIGS. 1A to 1C are a front view, side view, and perspective view of a tension measuring device of a first embodiment, respectively.

FIGS. 2A to 2C are a front view, side view, and perspective view of a first gel adaptor holder of the tension measuring device of the first embodiment, respectively.

FIGS. 4A to 4C are a front view, side view, and perspective view of a substrate that is used together with the tension measuring device of the first embodiment, respectively.

FIGS. 8A and 8B illustrate steps of producing the tension measuring device of the first embodiment, respectively.

FIG. 10A illustrates a mode of using a tension measuring system of the first embodiment, and FIG. 10B illustrates the tension measuring device that is connected to a tension detecting unit connector.

FIG. 12A illustrates a first gel adaptor holder, FIG. 12B illustrates a second gel adaptor holder, and FIG. 12C illustrates a combination of the first gel adaptor holder, the second gel adaptor holder, and a substrate.

FIGS. 15A and 15B illustrate results of measurements of the tension of human iPS cell-derived myocardial cells measured by using the tension measuring device of the presently disclosed subject matter, the results that were obtained in FIG. 14 are normalized by using the average value and are plotted, FIG. 15A illustrates results of measurements of the tension of myocardial cells that were detected by using Adaptor-1 (comparison example), and FIG. 15B illustrates results of measurements of the tension of myocardial cells that were detected by using Adaptor-2 (presently disclosed subject matter).

FIG. 29 is a perspective view illustrating a state where the rod is held by a rod holding jig.

DETAILED DESCRIPTION

First Embodiment

Figure 1B:
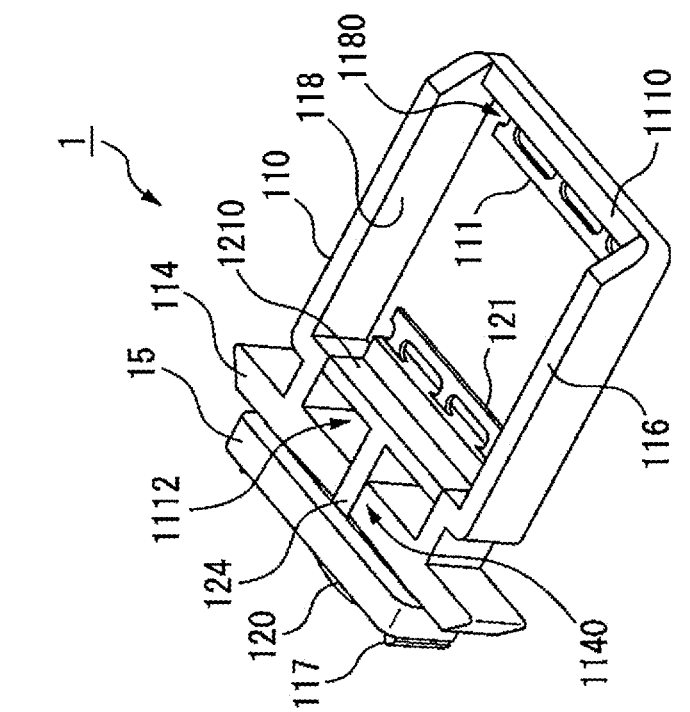

Hereinafter, a first embodiment of the presently disclosed subject matter will be described with reference to the drawings as required. The configuration of the embodiment is an example, and the configuration of the presently disclosed subject matter is not limited to the specific configuration of the embodiment.

<Cell Structure Containing Muscle Cells>

In the specification, "cell structure containing muscle cells" means living bodytissue (for example, myocardial tissues, skeletal muscle tissues, or smooth muscle tissues) containing muscle cells collected from the living body, or a structure containing muscle cells. The cell structure containing muscle cells that can be applied to the presently disclosed subject matter may be living bodytissue itself collected from the living body, or living bodytissue that is obtained by processing living bodytissue collected from the living body. Alternatively, the cell structure containing muscle cells that can be applied to the presently disclosed subject matter may be a cell structure that is formed by mixing a suspension containing muscle cells with a gel solution or a gelling agent, or a cell sheet. Alternatively, the cell structure containing muscle cells that can be applied to the presently disclosed subject matter may be a structure that is formed by directly seeding and culturing a cell group containing muscle cells on a gel.

In the embodiment, the cell structure containing muscle cells that can be applied to the presently disclosed subject matter may be at least one selected from a group consisting of a sheet-like shape, a rod-like shape, and a string-like shape, and preferably a sheet-like cell structure.

In the specification, "sheet-like cell structure" means a film-like cell structure having an average thickness of, for example, about 10 μm (e.g., the thickness of one cell) or more and about 2 mm or less, and having a length that enables the structure to be applied between first and second gel holding portions which will be described later. The width of "sheet-like cell structure" is requested to have a value that enables the structure to be applied to the first and second gel holding portions, and not particularly limited. One "sheet-like cell structure" may be applied to the tension measuring device, or a plurality of "sheet-like cell structures" may be applied to the tension measuring device. The plurality of "sheet-like cell structures" may be applied in parallel between the first and second gel holding portions, or applied in a stacked manner.

In the specification, "rod-like cell structure" means a cell structure having an average diameter of, for example, about 100 μM or more and about 5 mm or less, and having a length that enables the structure to be applied between the first and second gel holding portions which will be described later. One "rod-like cell structure" may be applied to the tension measuring device, or a plurality of "rod-like cell structures" may be applied to the tension measuring device. The plurality of "rod-like cell structures" may be applied in parallel between the first and second gel holding portions, or applied in a bundled manner.

In the specification, "string-like cell structure" means a three-dimensional cell structure having a mean diameter of, for example, about 10 μm or more and about 100 μm or less, and having a length that enables the structure to be applied between the first and second gel holding portions which will be described later. One "string-like cell structure" may be applied to a tension measuring device, or a plurality of "string-like cell structures" may be applied to a tension measuring device. The plurality of "string-like cell structures" may be applied in parallel between the first and second gel holding portions, or applied in a bundled manner.

Although, for the sake of convenience, "rod-like cell structure" and "string-like cell structure" are separately described depending on the diameter, both the terms mean a long thin shape cell structure, and may be exchangeably used.

For example, "rod-like cell structure" and "string-like cell structure" that can be applied to the presently disclosed subject matter may be produced by forming (for example, winding, twisting, constricting, or cutting) a sheet-like cell structure into a rod-like shape or a string-like shape, or by pouring a suspension containing cells and an arbitrary gel into a mold having a rod-like or string-like recess (for example, see Zhao Y Cell. 2019 Feb. 7; 176(4): 913-927).

In the specification, "cell structure containing muscle cells" means a cell structure that, with respect to the number of muscle cells contained in the cell structure, contains at least 10% or more of muscle cells. For example, muscle cells are contained at 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 95% or more, or 99% or more. In the specification, "muscle cells" means cells that form muscle tissue of an animal body, and that have contractility. Examples of such cells are myocardial cells, skeletal muscle cells, and smooth muscle cells. In the embodiment, "muscle cells" that is used in the presently disclosed subject matter is at least one selected from a group consisting of myocardial cells, skeletal muscle cells, and smooth muscle cells. The muscle cells that can be used in the presently disclosed subject matter are requested to be animal-derived. For example, muscle cells of a mammal, a bird, an amphibian, a reptile, or a fish can be used. Mammal-derived muscle cells are preferably used. For example, muscle cells derived from a mammal such as a mouse, a rat, a human, a monkey, a pig, a dog, a sheep, a cat, or a goat may be used.

Myocardial cells that can be used in the presently disclosed subject matter may be primary cells that are collected from living body tissue, or cell lines, or cells that are differentiated from pluripotent stem cells or tissue stem cells.

In the specification, "pluripotent stem cells" is intended to generally mean stem cells having the ability to differentiate into cells of any kind of tissue (pluripotent differentiation). Although not limited, the pluripotent stem cells include embryonic stem cells (ES cells), embryonic carcinoma cells (EC cells), trophoblast stem cells (TS cells), epiblast stem cells (EpiS cells), embryonic germ cells (EG cells), multipotent germline stem cells (mGS cells), induced pluripotent stem cells (iPS cells), Muse cells, or the like. Preferably, ES cells or iPS cells are used. Although, as the pluripotent stem cells, arbitrary known pluripotent stem cells can be used, pluripotent stem cells disclosed in, for example, WO/2009/123349 (PCT/JP2009/057041) may be used.

Muscle cells that can be used in the presently disclosed subject matter may be cells that are differentiated from pluripotent stem cells. As a method of differentiating from pluripotent stem cells to muscle cells, a known method can be used (for example, see Matsuura K., et al. Creation of human cardiac cell sheets using pluripotent stem cells. Biochem. Biophys. Res. Commun. 2012 Aug. 24; 425(2): 321-327).

The cell structure containing muscle cells may contain cells other than muscle cells. For example, cardiac myoblasts, myoblast cells, mesenchymal stem cells, vascular endothelial cells, vascular endothelial precursor cells, fibroblasts, and the like may be contained.

In the specification, "cell sheet" that is an embodiment of "sheet-like cell structure" means one or plural layers of sheet-like cell groups that are obtained by culturing a cell group containing a plurality of arbitrary cells on a cell culture substrate, and harvesting the cell group as an intact cell sheet from the cell culture substrate. Examples of the method of obtaining a cell sheet are: a method in which cells are cultured on a stimuli-responsive culture substrate coated with a polymer in which the molecular structure is changed by stimulation such as the temperature, the pH, or light, and the surface of the stimuli-responsive culture substrate is changed by changing conditions of the temperature, the pH, and light, whereby, while maintaining the cell-cell adhesion, the cells are harvested as an intact cell sheet from the stimuli-responsive culture substrate; and that in which cells are cultured on an arbitrary culture substrate, and the cells are physically peeled off from the substrate by using tweezers. As a stimuli-responsive culture substrate for obtaining a cell sheet, a temperature-responsive culture substrate is known in which the surface is coated with a polymer in which the hydration force is changed in a temperature range from 0° C. to 80° C. Cells are cultured on such a temperature-responsive culture substrate in a temperature range where the hydration force of the polymer is weak, and then the temperature of the culture solution is changed to a value at which the hydration force of the polymer is strong, whereby the cells can be harvested in the form of a sheet-like cell group.

Preferably, the temperature-responsive culture substrate that is used for obtaining a cell sheet is a substrate in which the hydration force of the surface is changed in a temperature range where the cells can be cultured. It is preferable that the temperature range includes a temperature at which cells are usually cultured, for example, from 33° C. to 40° C. The temperature-responsive polymer for coating the culture substrate that is used in order to obtain a cell sheet may be one of a homopolymer and a copolymer. An example of such a polymer is a polymer that is disclosed in, for example, JPH02-211865.

A case where poly(N-isopropylacrylamide) is used as the stimuli-responsive polymer, particularly, the temperature-responsive polymer (temperature-responsive culture dish) will be exemplarily described. Poly(N-isopropylacrylamide) is known as a polymer in which the lower critical solution temperature is 31° C., and, in a free state, dehydration is caused in water at a temperature of 31° C. or higher, and polymer chains aggregate to become cloudy. At a temperature of lower than 31° ° C., by contrast, polymer chains hydrate to become a state where the polymer dissolves in water. In the presently disclosed subject matter, the polymer is coated on and fixed to the surface of the substrate such as a petri dish. At a temperature of 31° C. or higher, therefore, also the polymer on the surface of the culture substrate dehydrates in the same or similar manner, but polymer chains are fixed to the surface of the substrate, and therefore the surface of the culture substrate exhibits hydrophobicity. At a temperature of lower than 31° C., by contrast, the polymer on the surface of the culture substrate hydrates, but polymer chains are coated on the surface of the culture substrate, and therefore the surface of the culture substrate exhibits hydrophilicity. At this time, the hydrophobic surface is a moderate surface to which cells are adhered, and can propagate itself, and the hydrophilic surface is a surface to which cells can not be adhered. When the substrate is cooled to lower than 31° C., therefore, cells separate from the surface of the substrate. In the case where cells are cultured until become confluent over the culture surface, when the substrate is cooled to lower than 31° C., a cell sheet can be recovered. The temperature-responsive culture substrate is not particularly limited as far as it exhibits the same effects. An example of the substrate is UpCell (registered trademark) that is commercially available from CellSeed Inc. (Tokyo, Japan).

<Tension Measuring Device>

The presently disclosed subject matter provides a device for measuring the tension of a cell structure containing muscle cells. The device includes:

a first gel adaptor holder that includes: a frame member; and a first gel holding portion that, for fixing one end of a gel, is disposed protrudingly from a part of a side inner surface of the frame member, the frame member including: a cutaway in an upper portion of the frame member at a position opposed to the first gel holding portion; and a pair of first grasping portions that are formed by the cutaway, an upper portion of the frame member having a pair of claw portions; and a second gel adaptor holder that includes: a second gel holding portion for fixing another end of the gel; and a connecting portion that is connected to the second gel holding portion through a coupling portion.

The second gel adaptor holder is attached to the first gel adaptor holder by causing the first grasping portions to grasp the coupling portion so that, inside the frame member, the second gel holding portion is opposed to the first gel holding portion.

A gap between the pair of first grasping portions is increased when the pair of claw portions are fitted to a cover of a culture medium tank.

FIGS. 1A to 6C illustrate a tension measuring device 1 of the embodiment of the presently disclosed subject matter, and a fastener 15, substrate 13, and gel forming cover 14 that are used together with the tension measuring device 1. The tension measuring device 1 may include a first gel adaptor holder 11 and a second gel adaptor holder 12. The first gel adaptor holder 11 may include a frame member 110, and a first gel holding portion 111 that, for fixing one end of a gel G (described later), is disposed protrudingly from a part of the side inner surface (an inner bottom surface 119 in FIG. 1A) of the frame member 110. The frame member 110 is formed by a frame member lower portion 1110, a frame member side portion 116 that is disposed perpendicularly from the both ends of the frame member lower portion 1110, and a frame member upper portion 114 that is disposed on end of the frame member side portion 116. In the embodiment, the frame member side portion 116 and the frame member upper portion 114 are thicker than the frame member lower portion 1110. The frame member 110 functions as a part of a formwork for forming the gel G, and plays a role of preventing any article from laterally contacting with the gel G and a cell structure CS. The existence of the frame member 110 allows the tension measuring device 1 to be easily attached to a culture medium tank cover 21 (described later) of a culture medium tank 2 while the shapes of the gel G and the cell structure CS are maintained.

First gel non-forming spaces 1180 are disposed between the both sides of the first gel holding portion 111 and the inner surface (side inner surface 118) of the frame member side portion 116, respectively. Gel shaping convex parts 131 of a substrate 13 that will be described later are fitted in the first gel non-forming spaces 1180, respectively.

The first gel holding portion 111 is disposed on the frame member lower portion 1110 so as to be parallel to a thin film of the gel G that is to be formed. One or more first gel holding ports 112 are disposed in the first gel holding portion 111. Moreover, first gel holding concave parts 113 may be disposed in the both ends of the first gel holding portion 111.

In the embodiment, the thicknesses of the frame member lower portion 1110 and a second gel holding portion coupling portion 1210 (described later) define the thickness of the gel G that is to be formed. When the thicknesses of the frame member lower portion 1110 and the second gel holding portion coupling portion 1210 are changed, therefore, it is possible to adequately change the thickness of the gel G. Although the thicknesses of the frame member lower portion 1110 and the second gel holding portion coupling portion 1210 are not limited, the thicknesses are requested to enable the cell structure containing muscle cells to be bonded, and stably held, and not to disturb a pulsating and contracting function of the cell structure containing muscle cells. For example, the thicknesses are from 0.5 mm to 3.0 mm, from 0.5 mm to 2.5 mm, from 0.5 mm to 2.0 mm, from 0.5 mm to 1.5 mm, from 1.0 mm to 3.0 mm, from 1.0 mm to 2.5 mm, from 1.0 mm to 2.0 mm, or from 1.0 mm to 1.5 mm. Preferably, the thicknesses are from 0.5 mm to 2.5 mm, and more preferably from 0.5 mm to 1.5 mm.

The first gel holding portion 111 is configured so as to be thinner than the frame member lower portion 1110 and the second gel holding portion coupling portion 1210. On the inner bottom surface 119, the first gel holding portion Ill is disposed at the intermediate position in the thickness direction of the frame member lower portion 1110. According to the configuration, the gel G covers the both surfaces or the upper and lower surfaces of the first gel holding portion 111, and is surely held.

The frame member 110 of the first gel adaptor holder 11 may include a cutaway 1143 in a part (the frame member upper portion 114) of the frame member 110 at a position opposed to the first gel holding portion 111 (see FIG. 2A). Because of the cutaway 1143, a pair of first grasping portions 1140 are formed in the frame member upper portion 114. The cutaway 1143 is disposed along the axial direction in which the first gel holding portion 111 and a second gel holding portion 121 are opposed to each other. The width of the cutaway 1143 is adequately adjusted in accordance with that of a coupling portion 124 of the second gel adaptor holder 12 to be combined.

A pair of first grasping portions 1140 grasp the coupling portion 124 of the second gel adaptor holder 12. This causes the second gel adaptor holder 12 to be attached to the first gel adaptor holder 11. Each of the first grasping portions 1140 may include a convex part 1141 that is protruded in the direction of grasping the coupling portion 124. In this case, a concave part 125 into which the convex parts 1141 are to be fitted is formed in the coupling portion 124 of the second gel adaptor holder 12. When the pair of first grasping portions 1140 grasp the coupling portion 124 of the second gel adaptor holder 12, the convex parts 1141 are fitted into the concave part 125, whereby the second gel adaptor holder 12 is prevented from slipping off from the first gel adaptor holder 11. According to the configuration, the gel that is formed in the tension measuring device 1 is prevented from being damaged, and furthermore the tension measuring device 1 is easily handled until a timing of measuring the tension of the cell structure containing muscle cells.

In the embodiment, the frame member upper portion 114 of the first gel adaptor holder 11 may have a pair of claw portions 117 that are disposed across the cutaway 1143. The pair of claw portions 117 are fitted to the culture medium tank cover 21 that will be described later, to fix the tension measuring device 1 to the culture medium tank cover 21. The pair of claw portions 117 are disposed in a manner that, when the claw portions are fitted to the culture medium tank cover 21, the gap between the pair of first grasping portions 1140 is increased (see FIG. 9C). According to the configuration, clearances are formed between the coupling portion 124 of the second gel adaptor holder 12 and the first grasping portions 1140, slidings between the coupling portion 124 and the first grasping portions 1140 are reduced, and the dispersion of measurement values due to slidings that are detected during the measurement of the tension of the cell structure containing muscle cells is reduced. The shapes and positions of the pair of claw portions 117 are requested to, when the claw portions are fitted to the culture medium tank cover 21, cause clearances to be formed between the coupling portion 124 and the first grasping portions 1140. As illustrated in FIGS. 2A to 2C, for example, the claw portions are inclined toward the frame member upper portion 114. In the embodiment, the pair of claw portions 117 are deformed according to their elasticity so as to be inserted into fitting portions 210 of the culture medium tank cover 21, and returned by the restoring force of the first gel adaptor holder to the original shape so as to be fixed to the culture medium tank cover 21.

The upper outer surface 1144 (see FIG. 2A) of the frame member upper portion 114 of the first gel adaptor holder 11 may be inclined toward the cutaway 1143. According to the configuration, when the tension measuring device 1 is fixed to the culture medium tank cover 21, the inclined surface of the upper outer surface 1144 is in contact with the inner surface of the culture medium tank cover 21, and gaps are formed between the coupling portion 124 of the second gel adaptor holder 12 and the first grasping portions 1140 (see FIG. 9C).

Figure 1A:
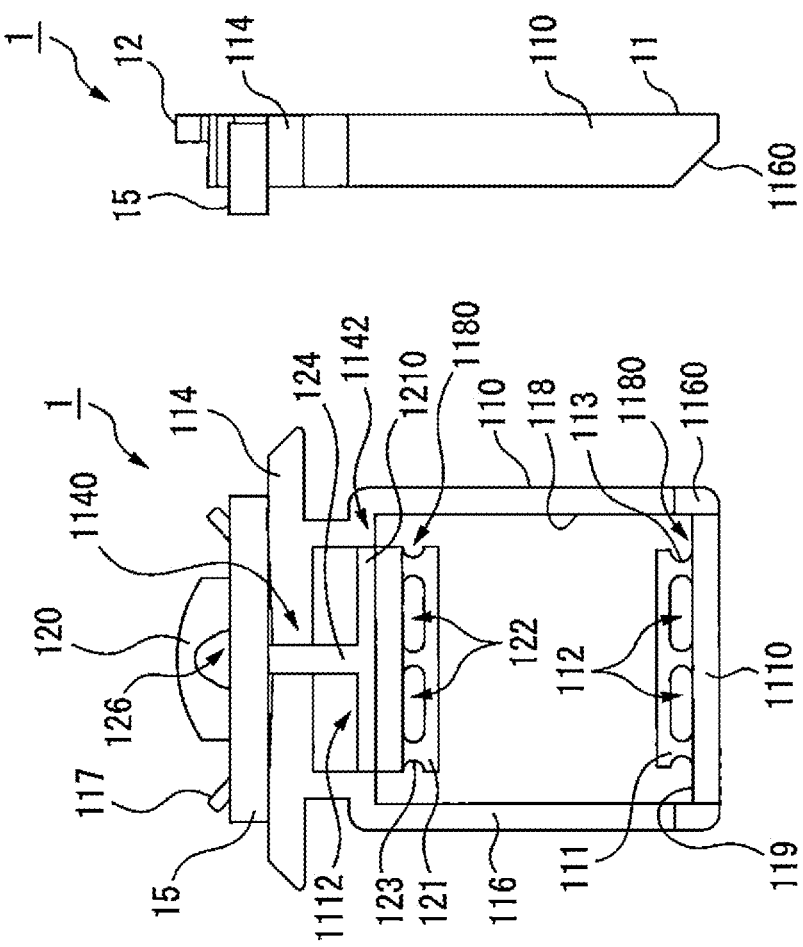

In the embodiment, the frame member 110 may further include a second grasping portion 1142 for grasping the second gel adaptor holder 12 (for example, see FIG. 1A). The second grasping portion 1142 may have a shape in which a part of the frame member 110 is inwardly recessed in accordance with the width of the second gel adaptor holder 12, for example, that of the second gel holding portion coupling portion 1210 (see FIG. 1A). According to the configuration, the second gel adaptor holder 12 can be fixed while being grasped by the second grasping portion 1142.

The material of the first gel adaptor holder 11 is not particularly limited as far as the material has a property which, when the pair of claw portions 117 are fitted to the culture medium tank cover 21, causes the gaps with respect to the first grasping portions 1140 to be widened. Examples of the material are polyethylene, polypropylene, polycarbonate, polystyrene, polyvinyl chloride, nylon, polyurethane, polyurea, polylactate, polyglycolic acid, polyvinyl alcohol, polyvinyl acetate, poly(meth)acrylic acid, a poly(meth)acrylic acid derivative, polyacrylonitrile, poly(meth)acrylamide, a poly(meth)acrylamide derivative, polysulfone, cellulose, a cellulose derivative, polysilicone, and a metal.

Figure 3A:
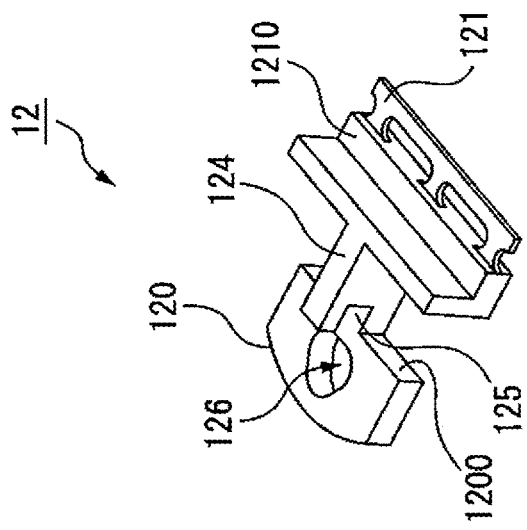
FIGS. 3A to 3C are a front view, side view, and perspective view of a second gel adaptor holder of the tension measuring device of the first embodiment, respectively.

The second gel adaptor holder 12 may include a second gel holding portion 121 for fixing the other end of the gel G, and a connecting portion 120 that is connected to the second gel holding portion 121 through the coupling portion 124 (see FIG. 3A). In the embodiment, as illustrated in FIG. 3A, the connecting portion 120 and the second gel holding portion 121 are joined to each other by the coupling portion 124 and the second gel holding portion coupling portion 1210. The second gel holding portion 121 is disposed on the second gel holding portion coupling portion 1210 so as to be parallel to the gel G that is to be formed. One or more second gel holding ports 122 are disposed in the second gel holding portion 121. Moreover, second gel holding concave pans 123 are disposed on the both ends of the second gel holding portion 121. The second gel holding portion 121 is configured so as to be thinner than the second gel holding portion coupling portion 1210, and preferably has the same thickness as that of the first gel holding portion 111. In the second gel holding portion coupling portion 1210, the second gel holding portion 121 is disposed at the intermediate position in the thickness direction. According to the configuration, the gel G covers the both surfaces or the upper and lower surfaces of the second gel holding portion 121, and is surely held.

Figure 3B:
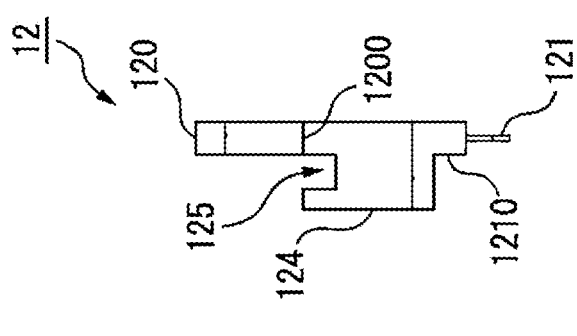
Figure 3C:
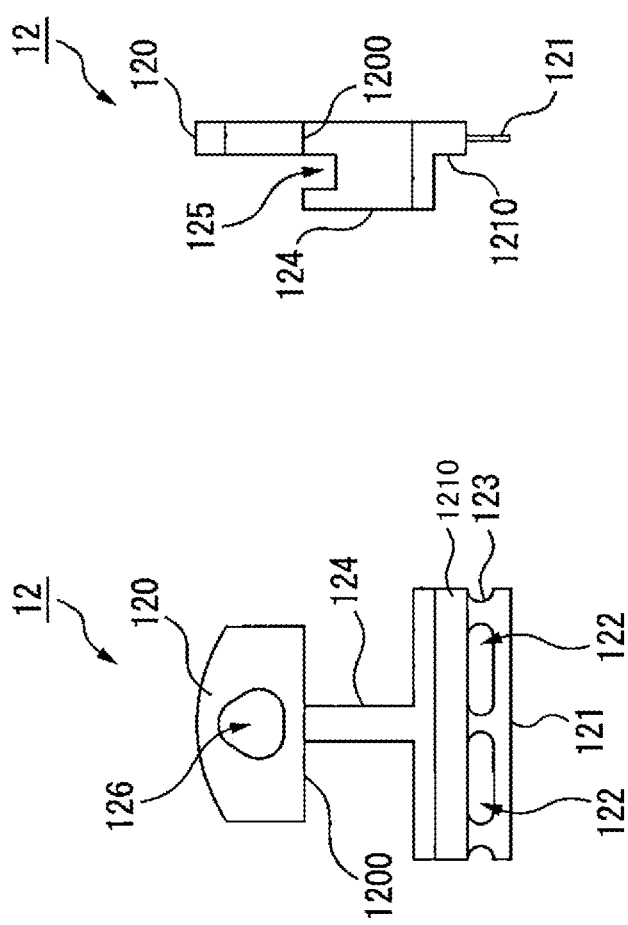

In the embodiment, the concave part 125 may be disposed into which the convex parts 1141 disposed on the first grasping portions 1140 of the first gel adaptor holder 11 are to be fitted, thereby preventing the second gel adaptor holder 12 from slipping off from the first gel adaptor holder 1 (see, FIGS. 3B and 3C). Particularly, the concave part 125 prevents the second gel adaptor holder 12 illustrated in FIG. 3A from anteroposteriorly slipping off from the first gel adaptor holder 11.

When the second gel adaptor holder 12 is attached to the first gel adaptor holder 11, the bottom (a connecting portion lower portion 1200) of the connecting portion 120 is contacted with the outer surface of the frame member upper portion 114. Therefore, a movement of the second gel adaptor holder 12 in the direction toward the first gel holding portion 111 (hereinafter, the direction is referred to as "downward direction") can be restricted, and the gel is prevented from being damaged. In the same or similar manner, also the second gel holding portion coupling portion 1210 is contacted with the outer surface of the frame member upper portion 114, and therefore a movement of the second gel adaptor holder 12 in the direction opposite to the first gel holding portion 111 (hereinafter, the direction is referred to as "upward direction") can be restricted, and the gel is prevented from being damaged. The movable range in the upward direction and downward direction (hereinafter, referred to as the upward/downward direction) of the second gel adaptor holder 12 can be adequately changed by adjusting the distance between the coupling portion lower portion 1200 and the second gel holding portion coupling portion 1210.

In the coupling portion 120, a connecting port 126 for coupling with a tension detecting unit connector 3 is disposed.

The gel that is poured into the first gel holding ports 112 and the second gel holding ports 122 is solidified, and thereafter performs a function of fixing the one end of the gel G to the first gel holding portion 111, and the other end to the second gel holding portion 121. Also the first gel holding concave parts 113 and the second gel holding concave parts 123 exert an effect of, after the gel is solidified, fixing the gel G. The numbers, shapes, and sizes of the first gel holding ports 112 and the second gel holding ports 122 are adequately determined depending on the size, gel viscosity, strength, polymerization degree, and the like of the gel G to be produced. The numbers of the first gel holding ports 112 and the second gel holding ports 122 may be, for example, from 1 to 10, from 1 to 5, from 2 to 5, or from 2 to 4. Preferably, the first gel holding portion 111 and the second gel holding portion 121 have a symmetrical shape.

Figure 6A:
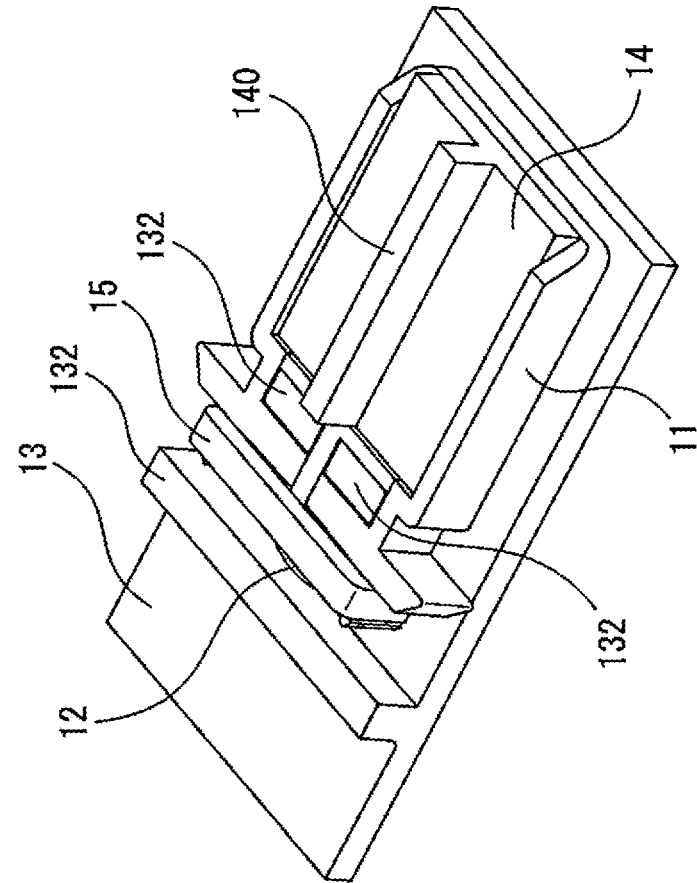
FIGS. 6A to 6C are a front view, side view, and perspective view of a combination of the members of FIGS. 2A to 5C and a gel forming cover, respectively.
Figure 6B:
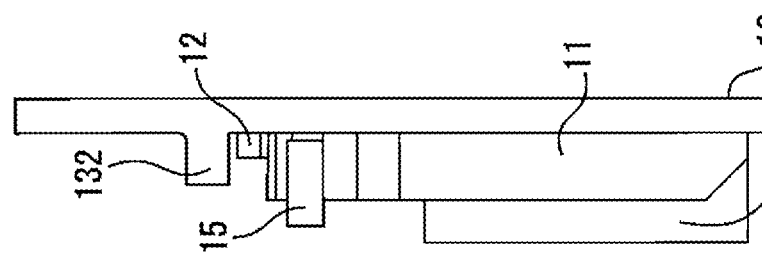
Figure 6C:
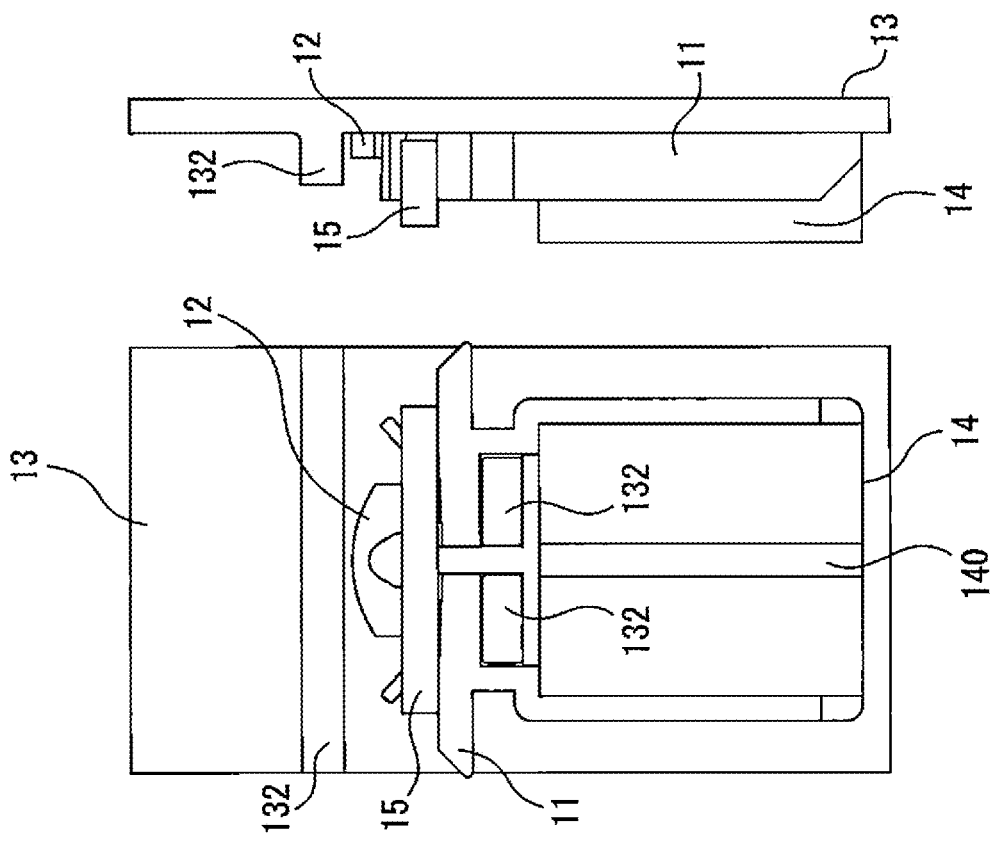

In order to form the gel G in the tension measuring device 1, the substrate 13 and the gel forming cover 14 are used (see FIGS. 4C and 6C). The pair of gel shaping convex parts 131 that are to be fitted between the first gel holding portion 111 and the second gel holding portion 121, and the side inner surface 118 are disposed on a planar portion 130 of the substrate 13. Gel forming convex upper parts 132 that are to be fitted into second gel non-forming spaces 1112 which are formed between the first gel adaptor holder 11 and the second gel adaptor holder 12 are disposed on the substrate 13. According to the configuration, the gel is not formed in the second gel non-forming spaces 1112.

The width of the gel forming cover 14 approximately coincides with the gap of the inner surfaces of the pair of gel shaping convex parts 131 that are disposed on the substrate 13. According to the configuration, the gel forming cover 14 is fitted between the pair of gel shaping convex parts 131. The length of the gel forming cover 14 in the embodiment is requested to enable the cover to cover the space in which the gel G is to be formed.

Figure 5C:
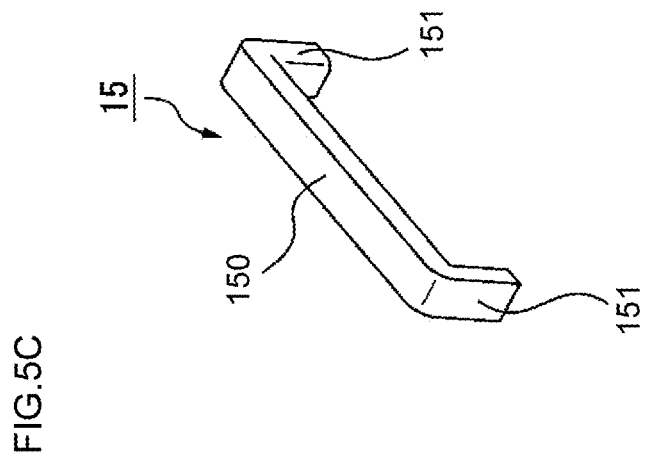
FIGS. 5A to 5C are a front view, side view, and perspective view of a fixing member that is used together with the tension measuring device of the first embodiment, respectively.
Figure 5B:
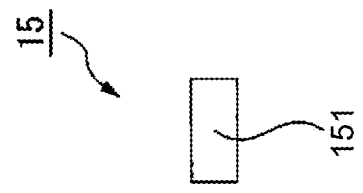
Figure 5A:
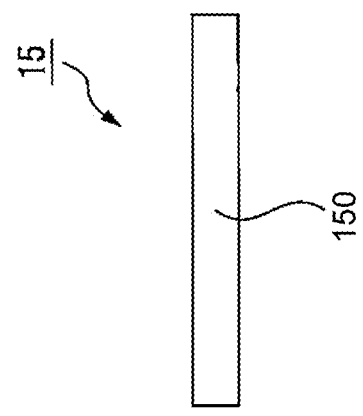

In the embodiment, the tension measuring device 1 of the presently disclosed subject matter may include the fastener 15 illustrated in FIGS. 5A to 5C. The fastener 15 may include a fastener body 150, and fastener legs 151 that are disposed substantially perpendicularly to the both ends of the fastener body 150. After the second gel adaptor holder 12 is attached to the first gel adaptor holder 11, the fastener 15 is attached so as to be engaged with the outer sides (fastener attaching portions 1170) of the pair of claw portions 117 (see FIG. 1A). When the fastener 15 is attached, an inward pressure is applied to the pair of first grasping portions 1140 of the frame member upper portion 114, and the second gel adaptor holder 12 is surely grasped. When the tension measuring device 1 is to be attached to the culture medium tank cover 21, for example, the fastener 15 is detached.

The materials of the second gel adaptor holder 12, the substrate 13, the gel forming cover 14, and the fastener 15 are not particularly limited. Examples of the materials are polyethylene, polypropylene, polycarbonate, polystyrene, polyvinyl chloride, nylon, polyurethane, polyurea, polylactate, polyglycolic acid, polyvinyl alcohol, polyvinyl acetate, poly(meth)acrylic acid, a poly(meth)acrylic acid derivative, polyacrylonitrile, poly(meth)acrylamide, a poly(meth)acrylamide derivative, polysulfone, cellulose, a cellulose derivative, polysilicone, glass, ceramics, and a metal.

<Kit for Producing Device for Measuring Tension of Cell Structure Containing Muscle Cells>

The presently disclosed subject matter provides a kit for producing the device for measuring tension of a cell structure containing muscle cells. The kit includes:

a first gel adaptor holder that includes: a frame member; and a first gel holding portion that, for fixing one end of a gel, is disposed protrudingly from a part of a side inner surface of the frame member, the frame member including: a cutaway in an upper portion of the frame member at a position opposed to the first gel holding portion; and a pair of first grasping portions that are formed by the cutaway, an upper portion of the frame member having a pair of claw portions;

a second gel adaptor holder that includes: a second gel holding portion for fixing another end of the gel; and a connecting portion that is connected to the second gel holding portion through a coupling portion;

a substrate that includes a pair of gel shaping convex parts which are fitted along the side inner surface of the frame member; and a gel forming cover that includes a surface which is parallel to a gel contacting surface of the substrate, in order to form an upper surface of the gel.

The second gel adaptor holder is attached to the first gel adaptor holder by causing the first grasping portions to grasp the connecting portion so that, inside the frame member, the second gel holding portion is opposed to the first gel holding portion, and A gap between the pair of first grasping portions is increased when the pair of claw portions are fitted to the culture medium tank cover.

The kit may include a gelling agent for producing the gel between the first gel holding portion and the second gel holding portion. The gelling agent that can be used in the presently disclosed subject matter means a material that can form a gel, and may be provided in the form of a solution or powder.

As the gel that can be used in the presently disclosed subject matter, a gel can be used as far as (1) a cell structure containing muscle cells can be adhered to the gel, (2) the gel has a strength that can maintain the sheet shape, and (3) the gel does not give an adverse effect on the growth of cells, the expression of a function, i.e., as far as the gel is biocompatible. An example of the gel that can be used in the presently disclosed subject matter is a hydrogel. Examples of the hydrogel that can be applied to the presently disclosed subject matter is a hydrogel in which a water-soluble, hydrophilic, or water-absorbing synthetic polymer such as polyacrylamide, polyacrylic acid, polyhydroxyethylmethacrylate, polyvinyl alcohol, polylactate, and polyglycolic acid, polysaccharide, protein, or nucleic acid is chemically linked. Examples of polysaccharide are glycosaminoglycan such as hyaluronic acid or chondroitin sulfuric acid, starch, glycogen, agarose, pectin, cellulose, and the like. Examples of protein are collagen, gelatin that is a hydrolysate of collagen, proteoglycan, fibronectin, vitronectin, laminin, entactin, tenascin, thrombospondin, a von Willebrand factor, osteopontin, fibrinogen (for example, a fibrin gel in which fibrinogen and thrombin are reacted with each other), and the like. Such a hydrogel may be used after applying a cross-linking treatment to the hydrogel by using a known method, to enhance the strength. Preferably, the gel that can be applied to the presently disclosed subject matter is a fibrin gel. In the embodiment of the presently disclosed subject matter, the gel may be obtained by mixing the gel with cells in advance.

<Method of Using Kit for Producing Device for Measuring Tension of Cell Structure Containing Muscle Cells>

A method of using the kit for producing a device for measuring the tension of a cell structure containing muscle cells in the embodiment will be described with reference to FIGS. 7A to 8B.

Figure 7A:
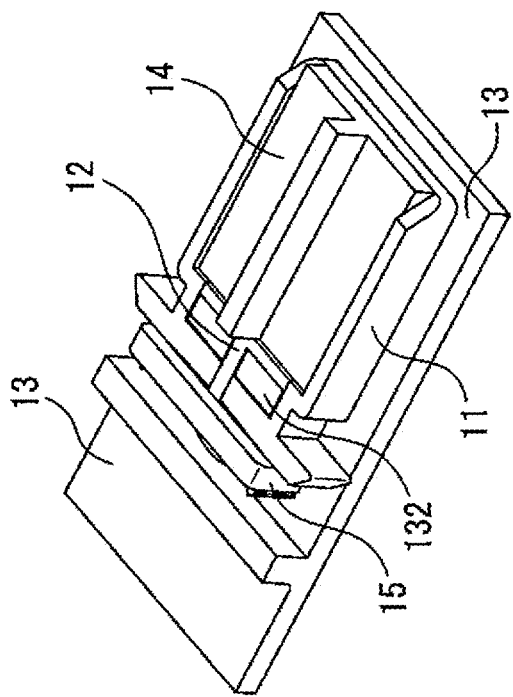
FIGS. 7A to 7C illustrate steps of producing the tension measuring device with using a kit for producing the tension measuring device of the first embodiment, respectively.

(i) The substrate 13 is set in the tension measuring device 1 (the first gel adaptor holder 11 and the second gel adaptor holder 12), and a gelling agent (for example, a mixture of fibrinogen (SIGMA, derived from bovine blood plasma, Type I-S), thrombin (SIGMA, derived from bovine blood plasma, T4648), a $CaCl_2$ solution (8 mM), and Factor XIII (CSL Behring, intravenous Fibrogamin P)) before curing is poured to a gel forming portion S by using a pipette P (FIG. 7A). At this time, the gel before curing is poured while paying careful attention not to allow the air to enter the first gel holding ports 112 and the second gel holding ports 122.

Figure 7B:
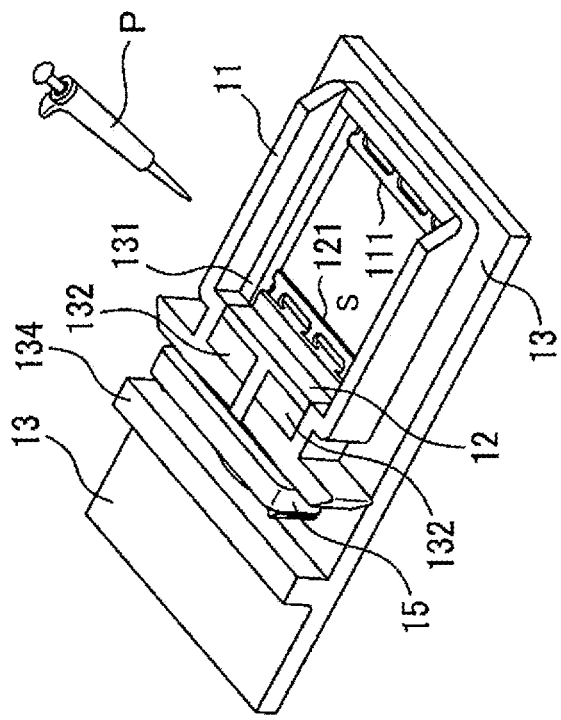

(ii) After pouring, the gel forming portion S is covered by the gel forming cover 14 (FIG. 7B).

Figure 7D:
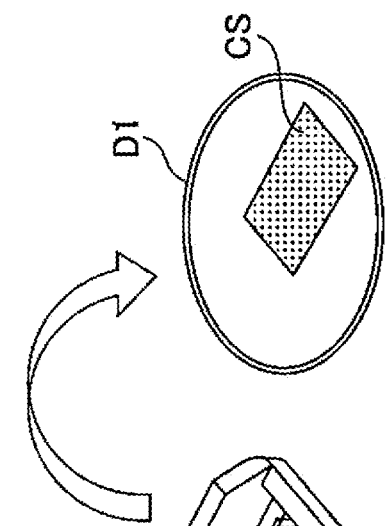
FIG. 7D is a sectional view of the tension measuring device that is obtained in FIG. 7C.
Figure 7C:
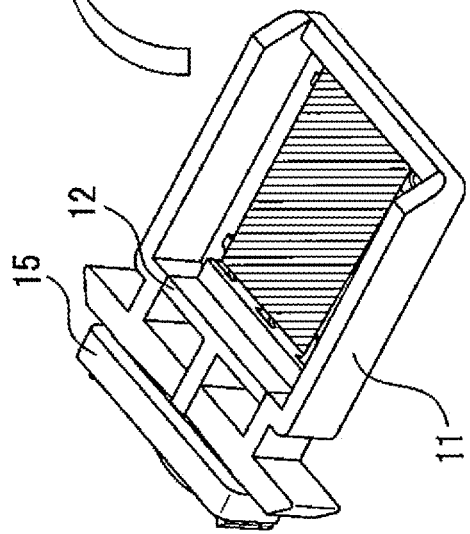

(iii) The gel is cured, and thereafter the gel forming cover 14 and the substrate 13 are detached from the tension measuring device 1 (FIG. 7C).

(iv) Separately from the above, a cell group containing muscle cells is seeded onto a temperature-responsive culture dish D1 (for example, UpCell (registered trademark), (CellSeed Inc., Tokyo, Japan)), and cells are previously cultured at 37° C. until becoming confluent.

(v) The tension measuring device 1 including the gel that is obtained as described above is placed on the cell structure CS containing muscle cells of the temperature-responsive culture dish D1 (FIG. 7C).

(vi) Thereafter, the temperature is maintained at a value that is equal to lower than the lower critical solution temperature of the temperature-responsive culture dish D1, for example, 20° C., the cell structure CS containing muscle cells is harvested from the temperature-responsive culture dish D1 as an intact cell sheet, and at the same time the cell structure CS containing muscle cells is bonded to the lower surface of the gel G (FIG. 7D).

A single layer of the cell structure CS containing muscle cells may be bonded to the gel G, or a plurality of layers of the cell structure may be bonded to the gel. Bonding of a plurality of the cell structure CS containing muscle cells is realized by repeating the processes of (v) and (vi) above an arbitrary number of times.

It is preferable that, before the cell structure CS containing muscle cells is bonded to the gel G, the cell structure previously has a shape that is identical with the shape of the gel G. Examples of a method of shaping the cell structure to a shape identical with that of the gel G are a method in which a cultured sheet-like cell group is cut by using a surgical knife or the like, and that in which cells are seeded by using molds M that previously restricts a region where cells are to be bonded, to the shape of the gel G (for example, see FIG. 8A). When the lower surface of the gel G is bonded onto the cell structure CS that is formed into the shape of the gel G, and that contains muscle cells, the cell structure CS containing muscle cells can be easily bonded to the gel G without causing the cell structure to contract (see FIG. 8B).

In another embodiment, the cell structure CS containing muscle cells may be formed by directly seeding a cell group containing muscle cells to the upper surface of the gel G that is formed in step (iii) above, and performing culturing at 37° C. until become confluent or subconfluent. As a result, it is possible to obtain the gel G to which the cell structure CS containing muscle cells is bonded.

The tension measuring device 1 of the presently disclosed subject matter may be provided in a form in which the gel G is formed between the first gel holding portion 111 and the second gel holding portion 121 in advance, by using the above-described use method. An article in which the cell structure CS containing muscle cells is bonded to the gel G may be provided.

<Tension Measuring System for Measuring Tension of Cell Structure Containing Muscle Cells>

The presently disclosed subject matter provides also a system for measuring the tension of a cell structure containing muscle cells. The system for measuring the tension of a cell structure containing muscle cells may include, for example, the followings:

(1) a device including: a first gel adaptor holder that includes: a frame member; and a first gel holding portion that, for fixing one end of a gel, is disposed protrudingly from a part of a side inner surface of the frame member, the frame member including: a cutaway in an upper portion of the frame member at a position opposed to the first gel holding portion; and a pair of first grasping portions that are formed by the cutaway, an upper portion of the frame member including a pair of claw portions; and a second gel adaptor holder that includes: a second gel holding portion for fixing another end of the gel; and a connecting portion that is connected to the second gel holding portion through a coupling portion, the second gel adaptor holder being attached to the first gel adaptor holder by causing the first grasping portions to grasp the coupling portion so that, inside the frame member, the second gel holding portion being opposed to the first gel holding portion, a gap between the pair of first grasping portions being increased when the pair of claw portions are fitted to a cover of a culture medium tank, and the device further including:

a gel disposed between the first gel holding portion and the second gel holding portion; and a cell structure containing muscle cells that is bonded to a lower surface of the gel;

(2) a body of the culture medium tank in which the device of (1) is to be immersed;

(3) a culture medium tank cover that includes fitting portions which are to be fitted to the pair of claw portions, and a connecting portion through port through which the connecting portion of the second gel adaptor holder is to be passed, and that covers the culture medium tank body;

(4) a tension detecting unit that is connected to the connecting portion of the second gel adaptor holder;

(5) a calculator that is connected to the tension detecting unit, and that applies a calculation to a signal detected by the tension detecting unit to calculate a tension; and (6) an outputting unit that displays a result of the calculation performed by the calculator.

Figure 9A:
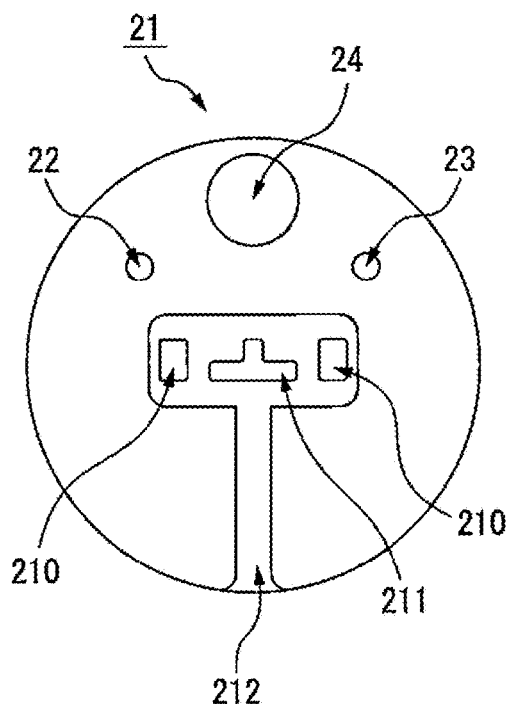
FIGS. 9A to 9D are a plan view, perspective view, front view, and side view of a mode of using the tension measuring device of the first embodiment, respectively.
Figure 9B:
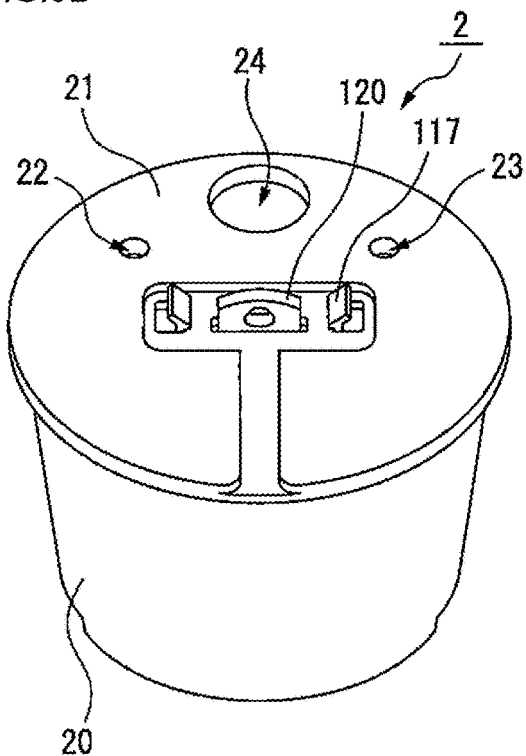
Figure 9C:
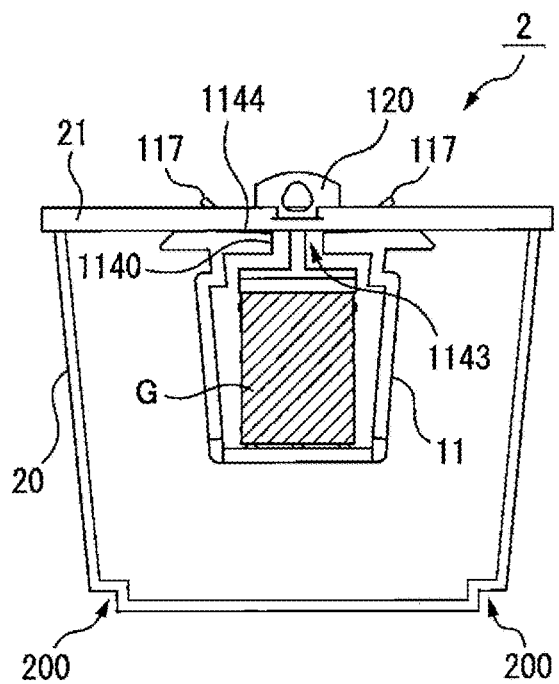
Figure 9D:
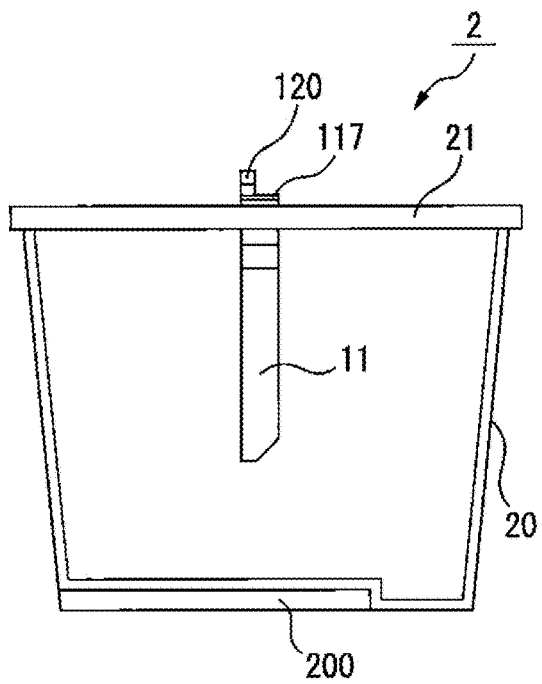

The tension measuring device including a gel and the cell structure containing muscle cells that is bonded to the gel is accommodated in the culture medium tank 2 (see FIGS. 9A to 9C). The culture medium tank 2 is configured by a culture medium tank body 20 and the culture medium tank cover 21. The culture medium tank cover 21 may include a culture medium supply line port 22 and a culture medium discharge line port 23. A culture medium supply line and a culture medium discharge line can be connected to the ports, respectively (not illustrated). According to the configuration, a culture medium in the culture medium tank 2 can be replaced with another one.

In the culture medium tank cover 21, the pair of fitting portions 210 into which the pair of claw portions 117 of the tension measuring device 1 are to be fitted are disposed. The fitting portions 210 are requested to have a shape that enables the cover to be connected to the device by the claw portions 117, and, for example, may be through ports as illustrated in FIG. 9A, or have a configuration where fitting units are disposed on the inner side of the culture medium tank cover 21 (not illustrated). The pair of fitting portions 210 are configured so that, when the portions are fitted to the pair of claw portions 117, the gap between the first grasping portions 1140 is increased (see FIG. 9C).

In the culture medium tank cover 21, a connecting portion through port 211 through which the connecting portion 120 of the second gel adaptor holder 12 is to be passed is disposed. The connecting portion through port 211 has a shape that allows the connecting portion 120 of the second gel adaptor holder 12 to pass through the cover.

In the culture medium tank cover 21, a sensor introduction port 24 may be further disposed. The sensor introduction port 24 enables an arbitrary sensor (for example, a pH sensor, a dissolved oxygen sensor, or a temperature sensor) to be introduced. In the culture medium tank cover 21, for example, a hook slide groove 212 that enables a hook 31 of the tension detecting unit connector 3 (described later) to be easily guided to the connecting port 126 of the second gel adaptor holder 12 may be further disposed (see FIGS. 9A and 9B).

The hook 31 of the tension detecting unit connector 3 is passed through the connecting port 126 of the second gel adaptor holder 12, and the culture medium tank 2 is disposed in a culturing system 4 (see FIGS. 10A and 10B). In the culture medium tank body 20, a culture medium tank concave part that enables a movement along guide rails 42 to be performed may be disposed so that the culture medium tank body is easily installed in the culturing system 4.

A tension detecting unit 40 is disposed in the culturing system 4. A tension detecting unit connecting portion 32 of the tension detecting unit connector 3 is connected to the tension detecting unit 40. When the cell structure CS containing muscle cells contracts, the second gel adaptor holder 12 is downward pulled, and the load is detected by the tension detecting unit through the tension detecting unit connector 3. A known load cell can be used as the tension detecting unit 40. According to the configuration, it is possible to measure a contracting force (tension) that is caused by pulsation of the cell structure CS containing muscle cells. The tension detecting unit connector 3 is requested to have a function of coupling the second gel adaptor holder 12 and the tension detecting unit 40 to each other, and may be configured by a clamping unit (not illustrated) in place of the hook 31.

Although not illustrated, a reagent supplying port may be further disposed in the culture medium tank cover 21. When an arbitrary medical agent is added through the reagent supplying port, an effect on muscle cells by the medical agent can be checked. Alternatively, a medical agent may be supplied into the culture medium tank 2 by adding the medical agent to a culture medium storing tank (not illustrated) connected to the culture medium supply line. Although not illustrated here, a culture medium may be supplied to the culture medium tank 2 by, for example, a tube pump, and the culture medium may be discharged by the tube pump.

A culture controller 41 of the culturing system 4 may include a heater so as to maintain the culture medium at a constant temperature. The culture controller may have a function of a magnetic stirrer. Therefore, the culture medium in the culture medium tank 2 can be stirred. In the culturing system 4, a hood (not illustrated) may be disposed in order to prevent a foreign material from entering the culture medium tank 2.

Figure 11:
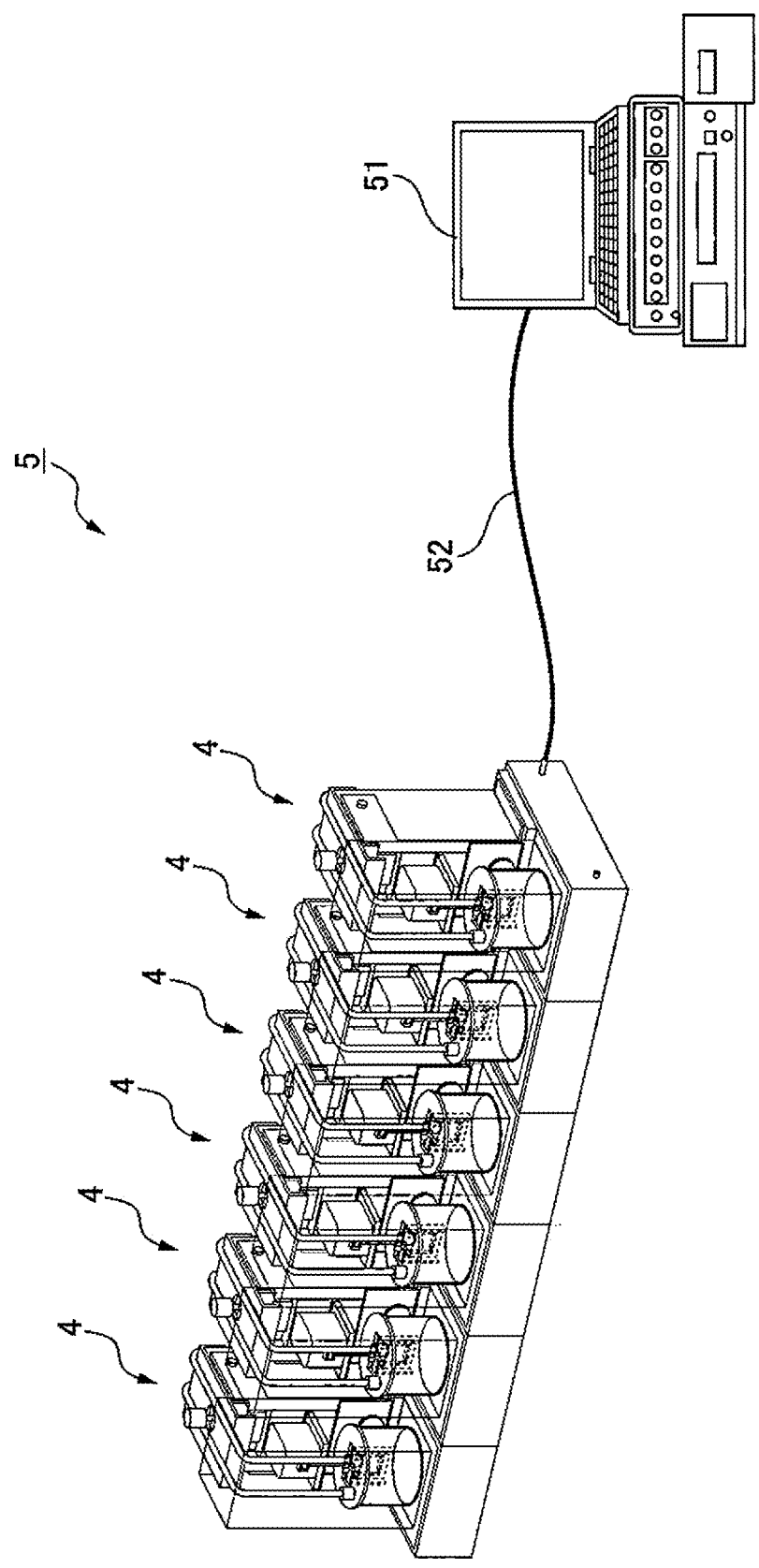
FIG. 11 illustrates the tension measuring system of the first embodiment of the presently disclosed subject matter.

FIG. 11 illustrates a tension measuring system 5 of the embodiment of the presently disclosed subject matter. The tension detecting units 40 of the culturing systems 4 in each of which the tension measuring device 1 is set are electrically connected to a calculator 51 through a cable 52. A signal that is detected by each of the tension detecting units 40 is supplied to the calculator 51 through the cable 52, and the calculator 51 performs calculation on the signal to calculate the tension. The calculation result is displayed by an outputting unit that is electrically connected to the calculator 51, such as a monitor.

Hereinafter, the presently disclosed subject matter will be described in further detail by means of examples, but it is not intended to limit the presently disclosed subject matter to the examples.

Example 1

1. Experimental Material and Method 1-1. Preparation of Myocardial Cell Sheet

A myocardial cell sheet containing iPS cell-derived myocardial cells was prepared in accordance with a method of Matsuura et al. (Matsuura K., et al. Creation of human cardiac cell sheets using pluripotent stem cells. Biochem. Biophys. Res. Commun. 2012 Aug. 24; 425(2): 321-327).

1-2. Tension Measuring Device

A tension measuring device (corresponding to the above-described tension measuring device 1) having a cutaway in the frame member of the first gel holding portion was used as the tension measuring device. In Example 1, the tension measuring device 1 made of a biocompatible resin (MED610, Stratasys Ltd.) was produced by a 3D printer (OBJET260 CONNEX 3, Stratasys Ltd.).

Figure 12B:
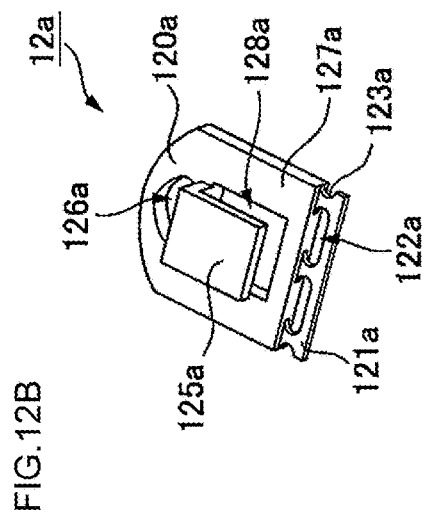
FIGS. 12A to 12C are perspective views of a tension measuring device of a comparison example.
Figure 12A:
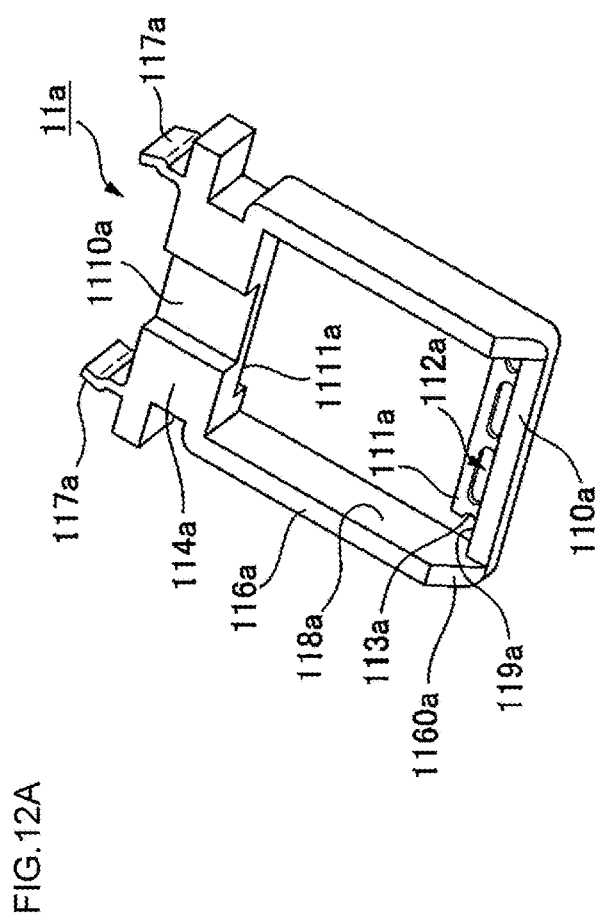
Figure 12C:
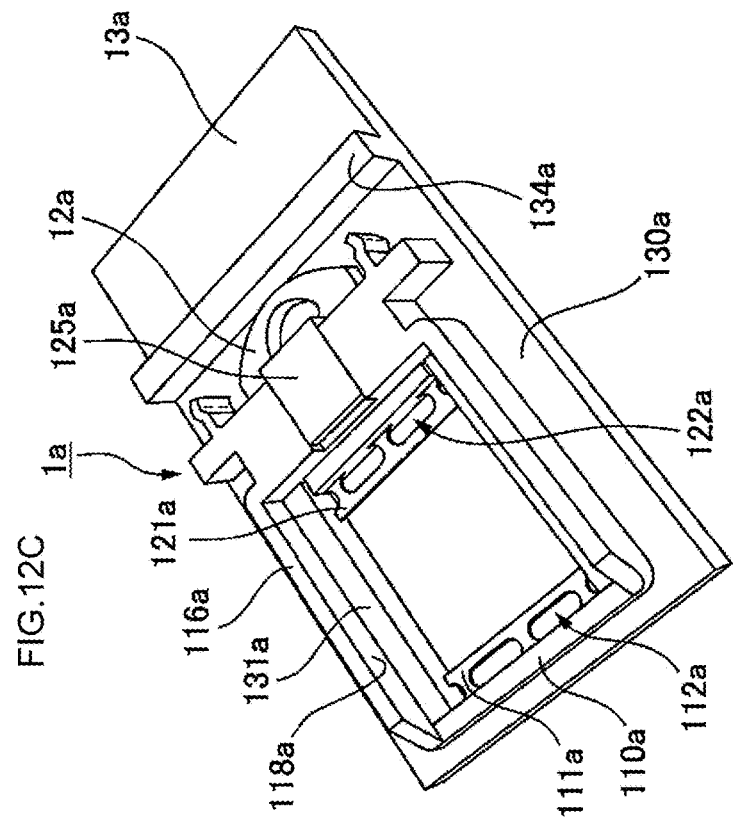

In order to verify the effect of the cutaway, a tension measuring device 1a (see FIGS. 12A to 12C) that does not have a cutaway was used as a comparative example.

The basic configuration of the tension measuring device 1a (a first gel adaptor holder 11a, a second gel adaptor holder 12a) is identical with that of the above-described tension measuring device 1. The above descriptions of the components of the tension measuring device 1 are applied to those of the corresponding components of the tension measuring device 1a except that "a" is affixed to the reference numerals of the components. Here, components to which the descriptions of the components of the tension measuring device 1 are not applied will be briefly described.

A frame member upper portion 114a of the first gel adaptor holder 11a includes a first guide groove 1110a and a second guide groove 1111a. Therefore, the sliding direction of the second gel adaptor holder 12a is restricted to the axial direction in which the first gel holding portion 111a and the second gel holding portion 121a are opposed to each other.

The second gel adaptor holder 12a includes an L-shaped member 125a. The L-shaped member 125a is fitted into the first guide groove 1110a, and a second gel adaptor body 127a is fitted into the second guide groove 1111a, whereby the second gel adaptor holder 12a is attached to the first gel adaptor holder 11a. In the tension measuring device 1a, therefore, the second gel adaptor holder 12a and the first gel adaptor holder 11a always slide even during use.

1-3. Measurement of Tension of Sheet-Like Cell Structure (Myocardial Cell Sheet) Containing Myocardial Cells The tension of the sheet-like cell structure containing myocardial cells was measured in the following procedure by using the tension measuring device 1 or the tension measuring device 1a of the comparative example (the reference numerals are omitted).

(i) The substrate was set in the tension measuring device (the first gel adaptor holder and the second gel adaptor holder), and a gelling agent (for example, a mixture of fibrinogen (SIGMA, derived from bovine blood plasma, Type I-S), thrombin (SIGMA, derived from bovine blood plasma, T4648), a $CaCl_2$ solution (8 mM), and Factor XIII (CSL Behring, intravenous Fibrogamin P)) before curing was poured to the gel forming portion by using a pipette.

(ii) After pouring, the gel forming portion was covered by the gel forming cover.

(iii) The gel was cured, and thereafter the gel forming cover and the substrate were detached from the tension measuring device.

(iv) Separately from the above, a cell group containing iPS cell-derived myocardial cells was seeded onto a temperature-responsive culture dish (UpCell (registered trademark), (CellSeed Inc., Tokyo, Japan)), and cells were previously cultured at 37° C. until becoming confluent.

(v) The tension measuring device including the gel that was obtained as described above was placed on the sheet-like cell structure containing myocardial cells.

(vi) Thereafter, the temperature of the temperature-responsive culture dish was maintained at 20° C., and the cell structure containing myocardial cells (hereinafter, referred to as a myocardial cell sheet) was bonded to the lower surface of the gel.

(vii) In a state where the tension measuring device to which the myocardial cell sheet was bonded was immersed in a medium for culture of myocardium (High glucose Dulbecco's Modified Eagle's Medium (DMEM, Wako 043-30085) to which 10% of fetal bovine serum (FBS, NICHIREI BIOSCIENCES INC.), 500 KIU/ml of aprotinin (Wako 016-11836), and 1% of penicillin-streptomycin (Wako 161-23181) were added), myocardial cells were cultured for one month under 37° C. and 5% of $CO_2$.

(viii) The tension measuring device illustrated in FIG. 10A was structured by using the tension measuring device to which the myocardial cell sheet was bonded, and the tension was measured.

2. Result

Figure 13:
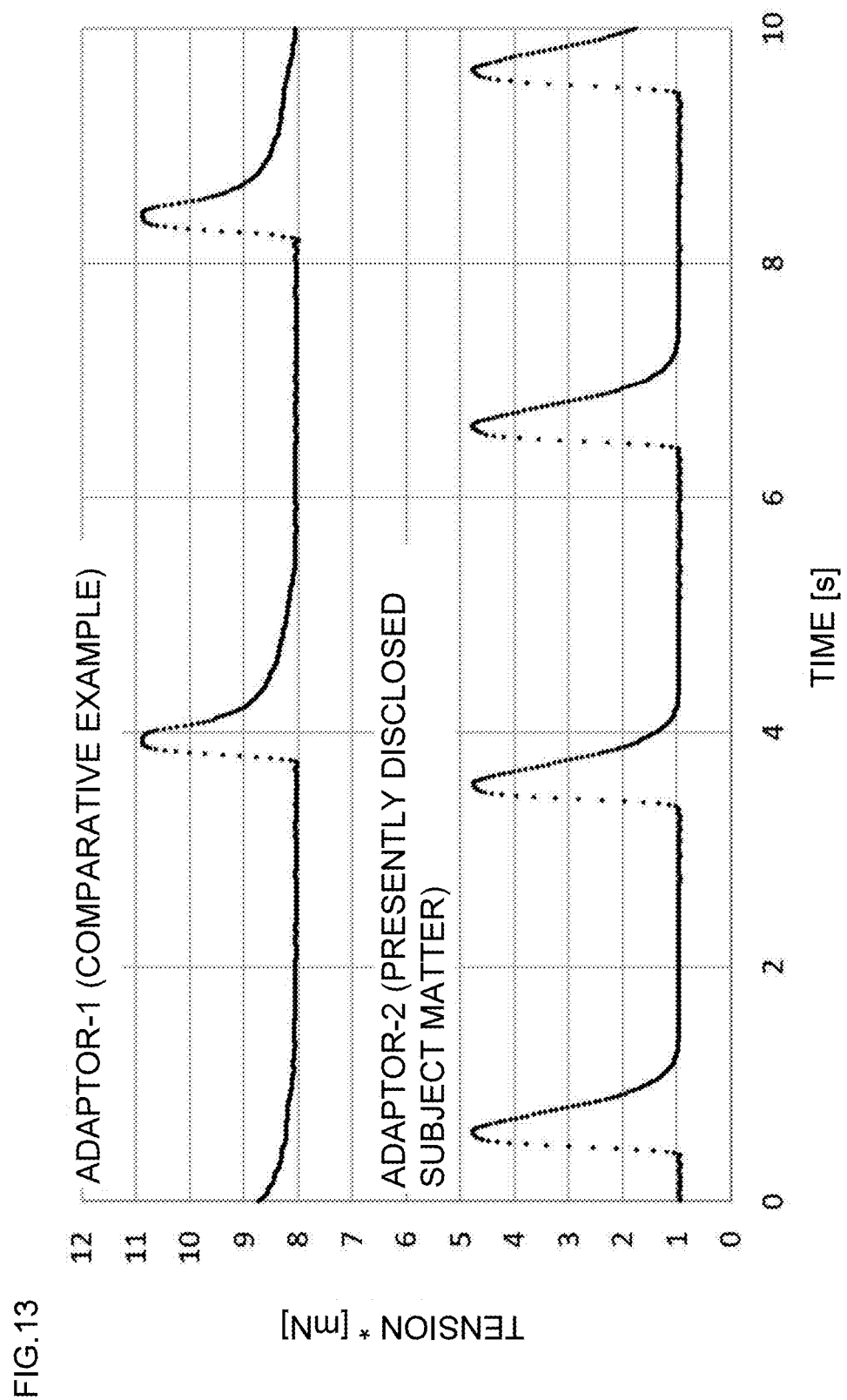
FIG. 13 illustrates results of measurements (10 seconds) of the tension of human iPS cell-derived myocardial cells measured by using the tension measuring device of the presently disclosed subject matter (Adaptor-2; lower plots). Results of measurements of the tension of myocardial cells that were detected by using Adaptor-1 (comparison example) are also illustrated (upper plots) for comparison. Note that, to compare them in the same graph, the base tensions are arbitrary shifted along the vertical axis.
Figure 14:
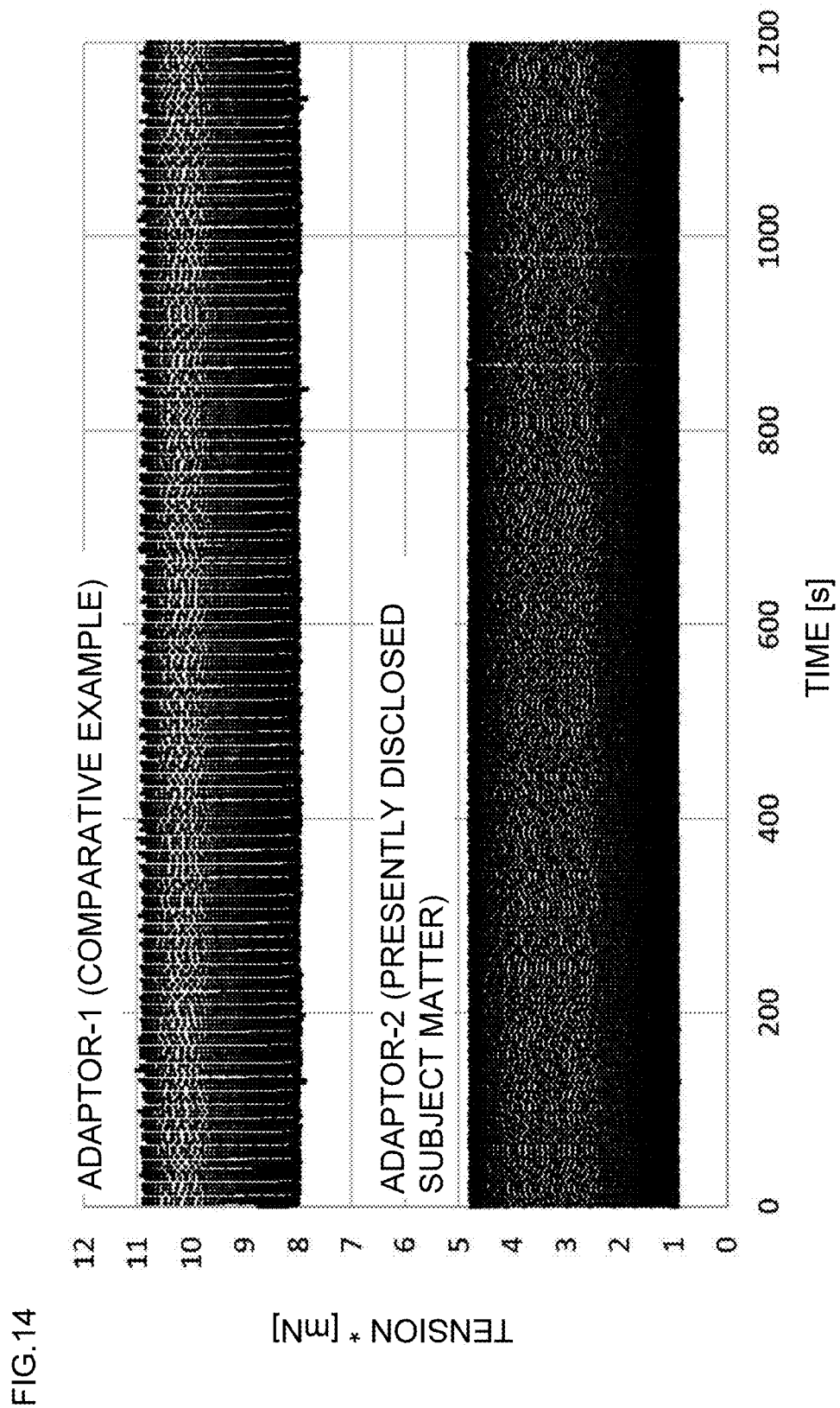
FIG. 14 illustrates results of measurements (1,200 seconds) of the tension of human iPS cell-derived myocardial cells measured by using the tension measuring device of the presently disclosed subject matter (Adaptor-2; lower plots). Results of measurements of the tension of myocardial cells that were detected by using Adaptor-1 (comparison example) are also illustrated (upper plots) for comparison. Note that, to compare them in the same graph, the base tensions are arbitrary shifted along the vertical axis.

It was seen that, in the myocardial cell sheet that was subjected to measurement by using the tension measuring device 1, the dispersion of the tension (corresponding to the widths of the bands in FIGS. 13 and 14) per pulsation (stroke) is reduced as compared with the case where the tension measuring device that does not have a cutaway was used (FIGS. 15A and 15B).

Example 2

Figure 16:
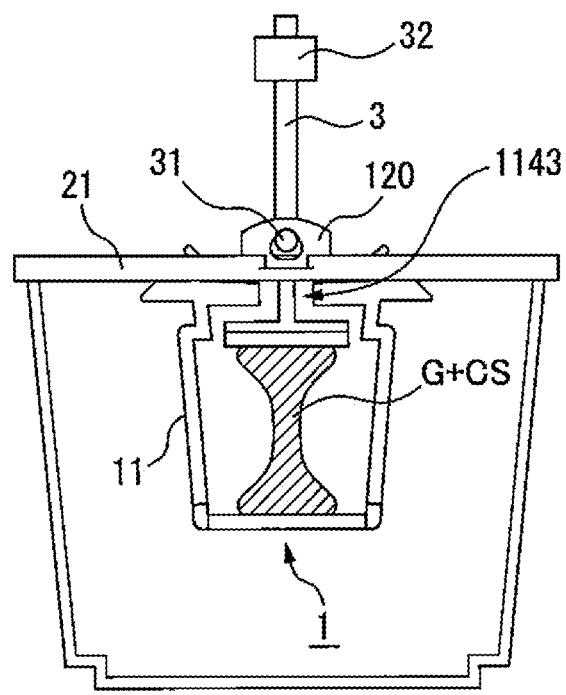
FIG. 16 illustrates a state where a rod-like cell structure containing human iPS cell-derived myocardial cells is applied to the tension measuring device of the presently disclosed subject matter.

A tension measuring device to which the myocardial cell sheet was bonded was obtained in accordance with (i) to (vi) described in 1-3 of Example 1. In this case, the tension measuring device 1 that is made of polypropylene was used. By using a tension measuring device that includes a myocardial cell tissue body, the myocardial cell tissue body was cultured in a medium for culture of myocardium for a long term (one month or longer) under 37° C. and 5% of $CO_2$. As a result, a rod-like myocardial cell tissue body in which the diameter in the vicinity of the center is about 100 to 200 μm was formed (FIG. 16).

The tension measuring system illustrated in FIG. 10A was constructed by using tension measuring device that includes the rod-like myocardial cell tissue body. As a result, the tension was measured without causing any problem.

Second Embodiment

Next, a second embodiment of the presently disclosed subject matter will be described with reference to FIGS. 17 to 33. With respect to portions that are common to the first embodiment, their description will be omitted, and those that are characteristic only in the second embodiment will be described.

FIGS. 17 to 33 illustrate a tension measuring device 6 of the second embodiment of the presently disclosed subject matter, and connecting members 66, substrate 67, gel forming cover 68, rod holding jig 69, rear cover 70, front cover 71, and the like that are used together with the tension measuring device 6.

As illustrated in FIGS. 17 to 23B, the tension measuring device 6 of the second embodiment may include a first gel adaptor holder 61 that fixes one end of a gel, a second gel adaptor holder 62 that fixes the other end of the gel, a rod 63 that connects the tension detecting unit 40 and the second gel adaptor holder 62 to each other, a fixing member (in the embodiment, for example, a pin 64) that connects the second gel adaptor holder 62 and the rod 63 to each other, and a culture medium tank 65 in which the first gel adaptor holder 61 and the second gel adaptor holder 62 are accommodated. Hereinafter, the components will be described in detail.

Figure 17:
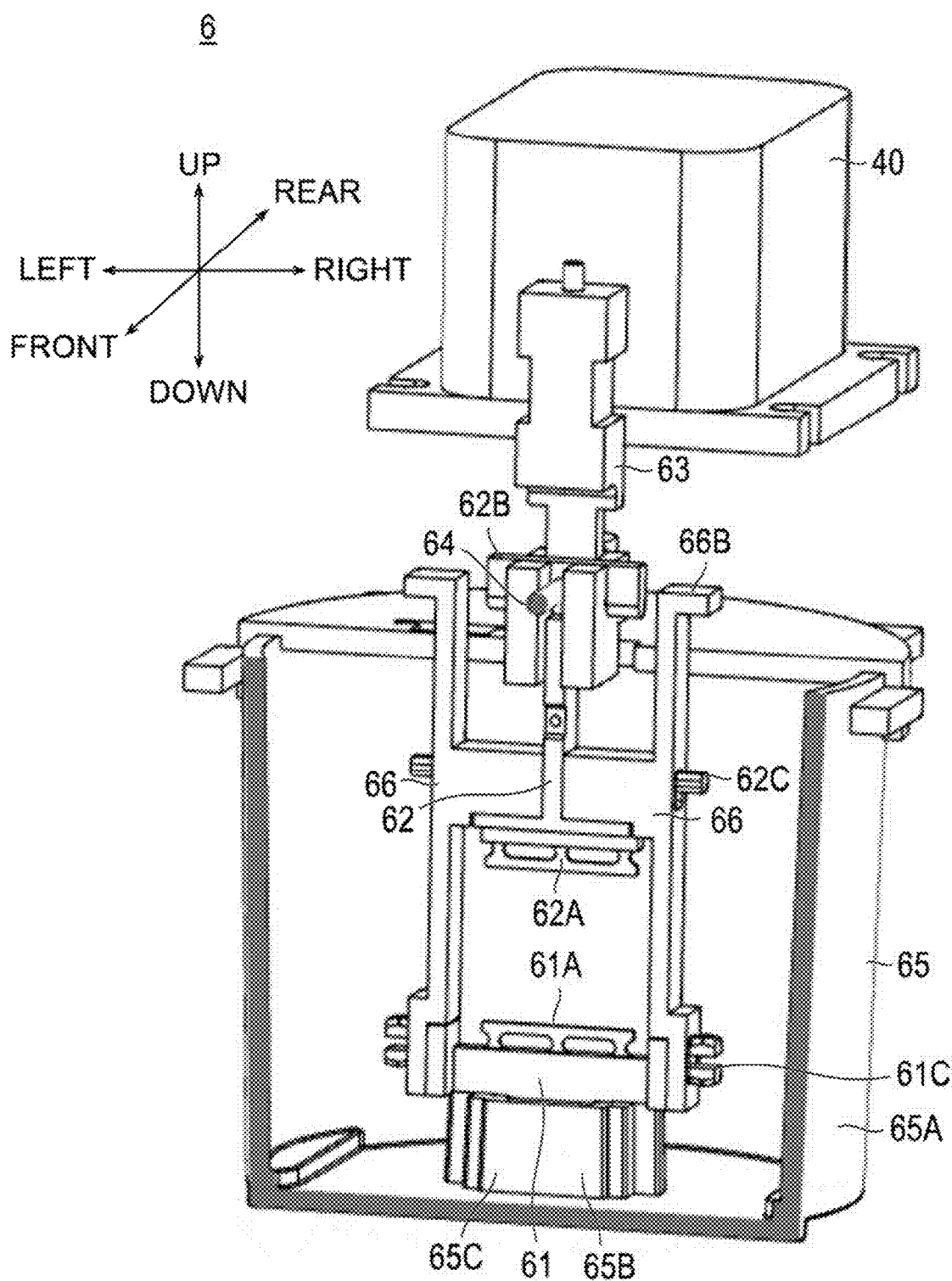
FIG. 17 is a perspective view illustrating a manner in which connecting members are connected to a tension measuring device of a second embodiment.
Figure 18A:
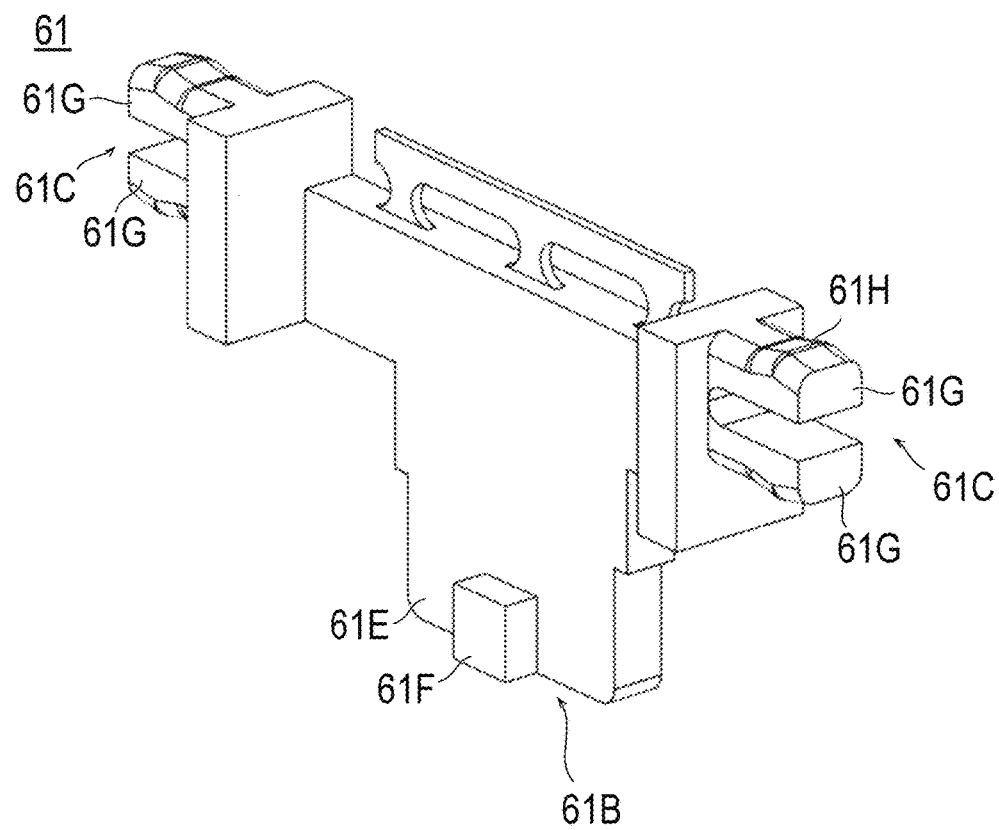
FIGS. 18A and 18B are a perspective view and front view illustrating a first gel adaptor holder of the tension measuring device of the second embodiment.
Figure 18B:
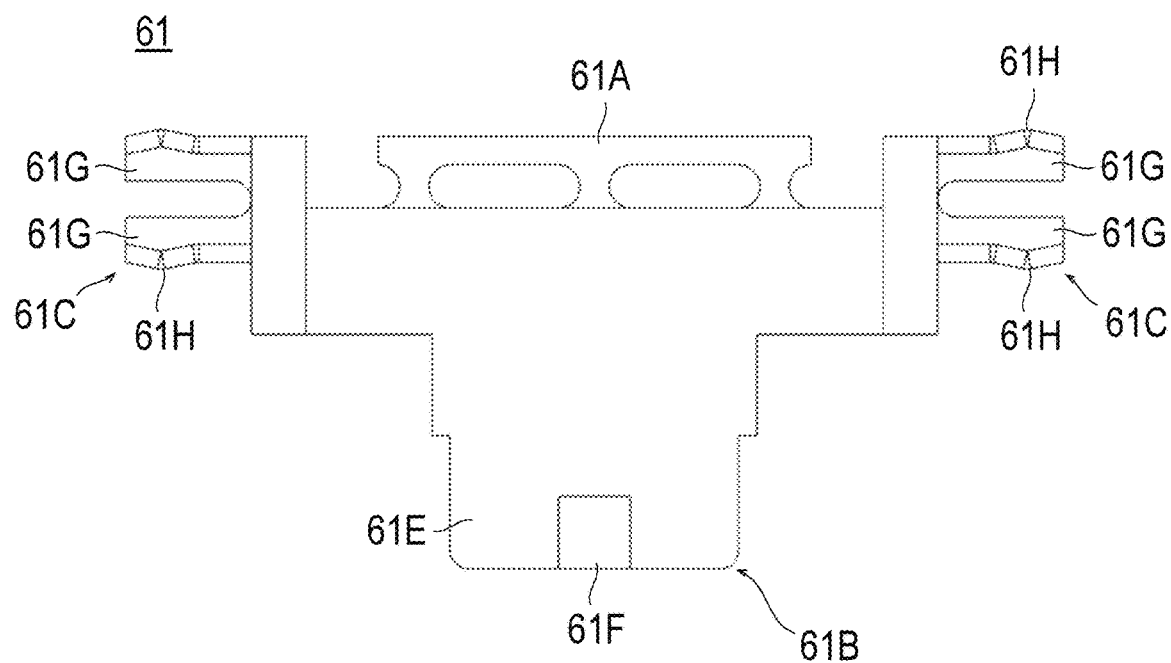

As illustrated in FIG. 17, the first gel adaptor holder 61 is placed so as to be fixed to the culture medium tank 65. As illustrated in FIGS. 17 to 18B, the first gel adaptor holder 61 may include a first gel holding portion 61A, a first fitting portion 61B, and fixing portions 61C.

The first gel holding portion 61A is placed to be opposed to a second gel holding portion 62A of the second gel adaptor holder 62 that will be described later. The configuration of the first gel holding portion 61A in the second embodiment is identical with that of the first gel holding portion 111 in the above-described first embodiment, and therefore its description will be omitted.

The first fitting portion 61B is configured so as to be fitted into a second fitting portion 65B of the culture medium tank 65 that will be described later. As illustrated in FIGS. 18A and 18B, the first fitting portion 61B may include a first protruding portion 61E that protrudes in the vertically downward direction, and a second protruding portion 61F that is disposed in a lower area of the first protruding portion 61E, and that protrudes in the direction toward the front side of a paper sheet. Although the illustration is omitted, a recess is formed in the second protruding portion 61F on the rear side of the paper sheet.

A pair of fixing portions 61C are disposed on the both lateral sides of the first gel holding portion 61A. The fixing portions 61C are configured so that the connecting members 66 that connect the first gel adaptor holder 61 and the second gel adaptor holder 62 to each other can be fixed. In the second embodiment, as illustrated in FIGS. 18A and 18B, each of the fixing portions 61C is configured by a pair of elastic members 61G that are elastically deformable. In the elastic members 61G, the elastic member 61G that is disposed in the upper side has a wide part 61H that is upwardly increase in thickness, and the elastic member 61G that is disposed in the lower side has a wide part 61H that is downwardly increase in thickness. According to the thus configured fixing portions 61C, when the fixing portions 61C are passed respectively through second through holes 66G of the connecting members 66 that will be described later, the fixing portions 61C are engaged with the second through holes 66G of the connecting members 66, and the connecting members 66 are fixed to the first gel adaptor holder 61.

Figure 19A:
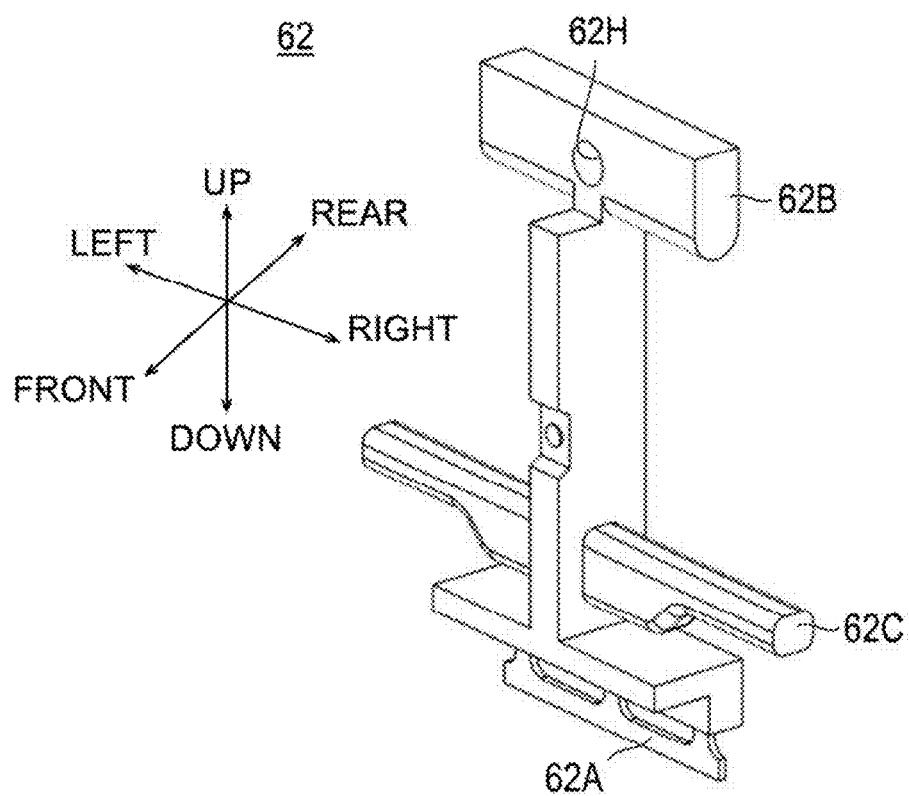
FIGS. 19A and 19B are a perspective view and front view illustrating a second gel adaptor holder of the tension measuring device of the second embodiment.
Figure 19B:
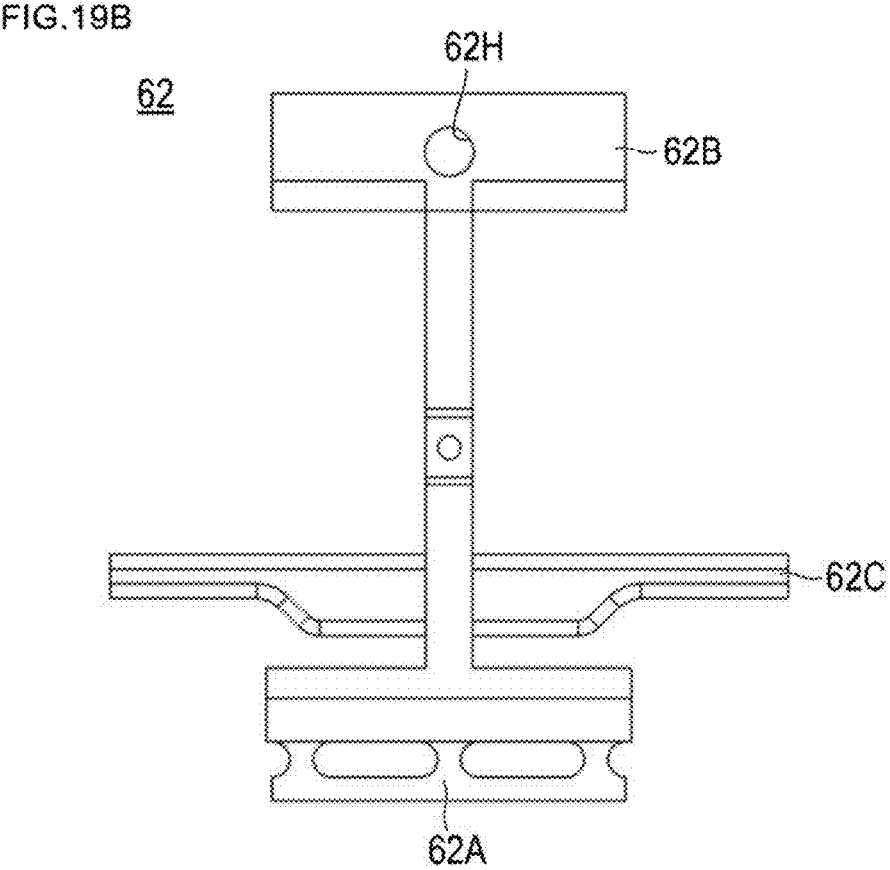

As illustrated in FIG. 17, the second gel adaptor holder 62 is placed above the first gel adaptor holder 61. As illustrated in FIGS. 17, 19A, and 19B, the second gel adaptor holder 62 may include a second gel holding portion 62A, a first elongated portion 62B, and sleeve portions 62C.

The second gel holding portion 62A is placed to be opposed to the first gel holding portion 61A. The configuration of the second gel holding portion 62A in the second embodiment is identical with that of the second gel holding portion 121 in the above-described first embodiment, and therefore its description will be omitted.

The first elongated portion 62B is disposed in the upper end that is opposite to the second gel holding portion 62A. As illustrated in FIGS. 19A and 19B, the first elongated portion 62B and the second gel holding portion 62A are configured so as to be elongated in the lateral direction. The upper part of the first elongated portion 62B is configured into a rectangular shape, and the lower part into a circular shape.

As illustrated in FIGS. 19A and 19B, the first elongated portion 62B may include a through hole 62H. The pin 64 is passed through the through hole 62H. The through hole 62H is configured so that its diameter is slightly larger than the outer diameter of the pin 64.

As illustrated in FIGS. 19A and 19B, a pair of sleeve portions 62C are disposed on the both lateral sides. The sleeve portions 62C are elongated in the lateral direction. The sleeve portions 62C are passed through first through holes 66H of the connecting members 66 that will be described later, respectively.

Figure 20A:
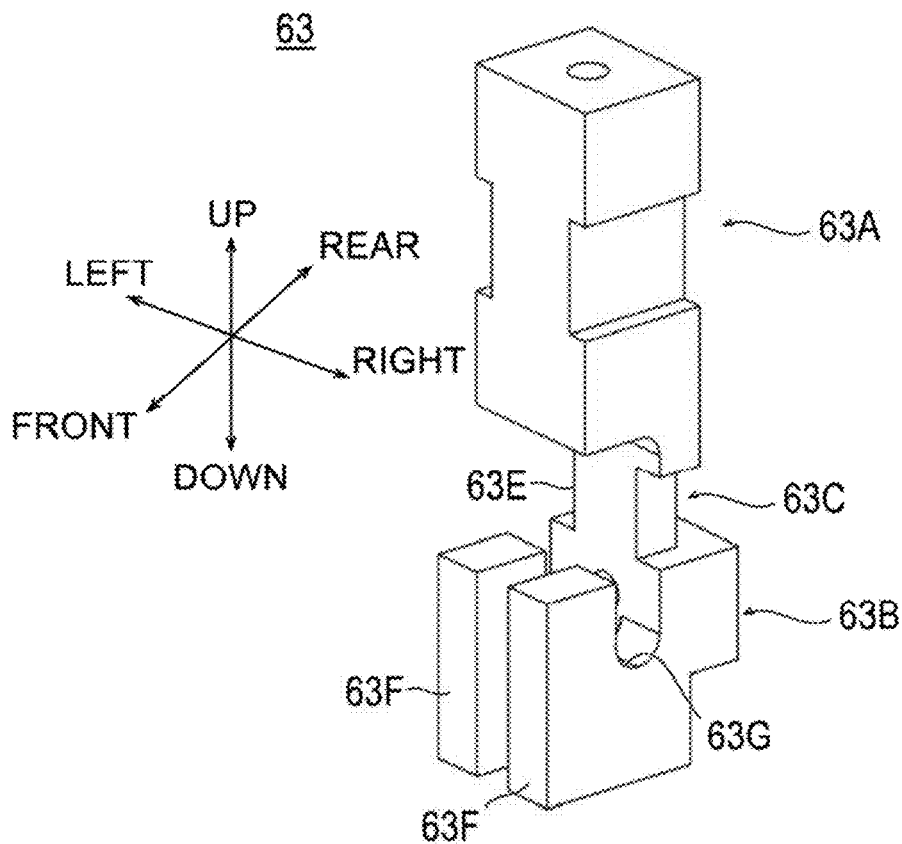
FIGS. 20A and 20B are a perspective view and front view illustrating a rod of the tension measuring device of the second embodiment.
Figure 20B:
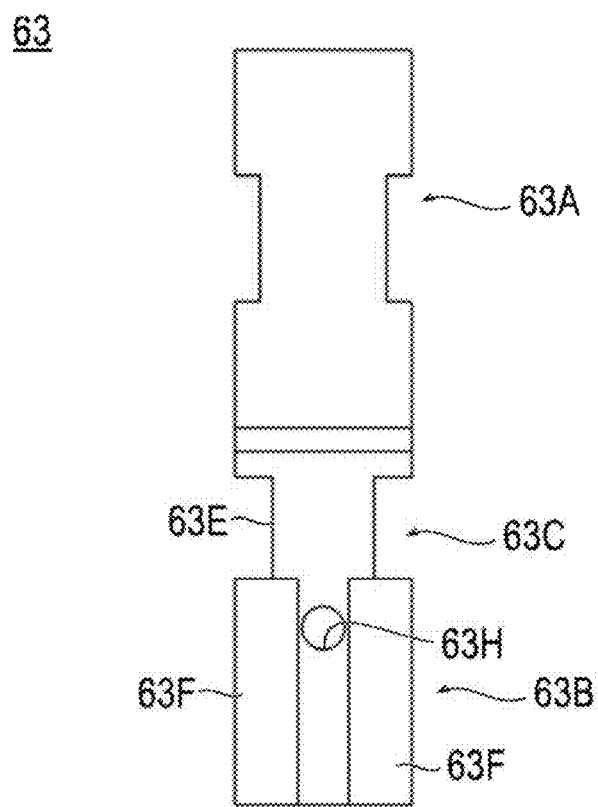

As illustrated in FIG. 17, the rod 63 connects together the tension detecting unit 40 and the second gel adaptor holder 62. The rod 63 is placed above the second gel adaptor holder 62. The rod 63 in the second embodiment corresponds to the tension detecting unit connector in the first embodiment. As illustrated in FIGS. 20A and 20B, the rod 63 is elongated in the vertical direction. The rod 63 may include an upper portion 63A that is disposed in the upper side, a lower portion 63B that is disposed in the lower side, and an intermediate portion 63C that is disposed between the upper portion 63A and the lower portion 63B.

A constricted part 63E that is inwardly recessed in the lateral direction is disposed in the intermediate portion 63C. A rod holding portion 69D of the rod holding jig 69 that will be described later is engaged with the constricted pan 63E. Therefore, the rod holding jig 69 holds the rod 63.

As illustrated in FIGS. 20A and 20B, the lower portion 63B may include halved portions 63F that are paired in the lateral direction, a recess 63G, and a through hole 63H. The recess 63G is disposed in the rear of the upper surfaces of the halved portions 63F. In the front view, the through hole 63H is disposed between the pair of halved portions 63F.

Figure 22A:
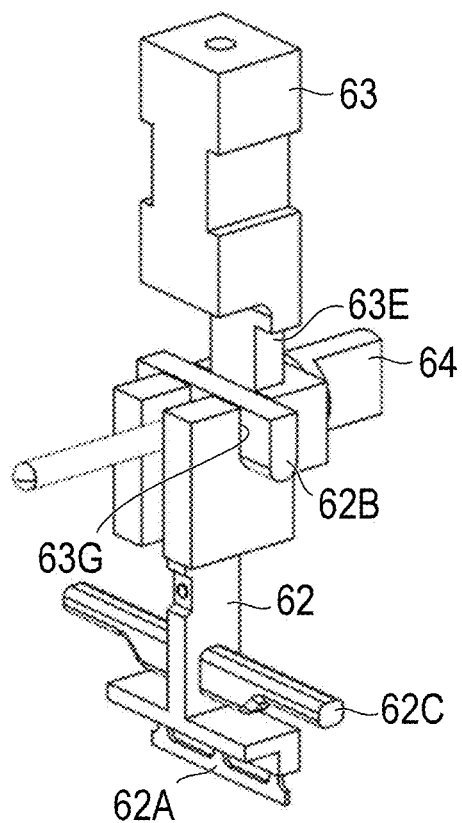
FIGS. 22A and 22B are a perspective view and side view illustrating a manner in which the second gel adaptor holder, rod, and pin of the tension measuring device of the second embodiment are assembled together.
Figure 22B:
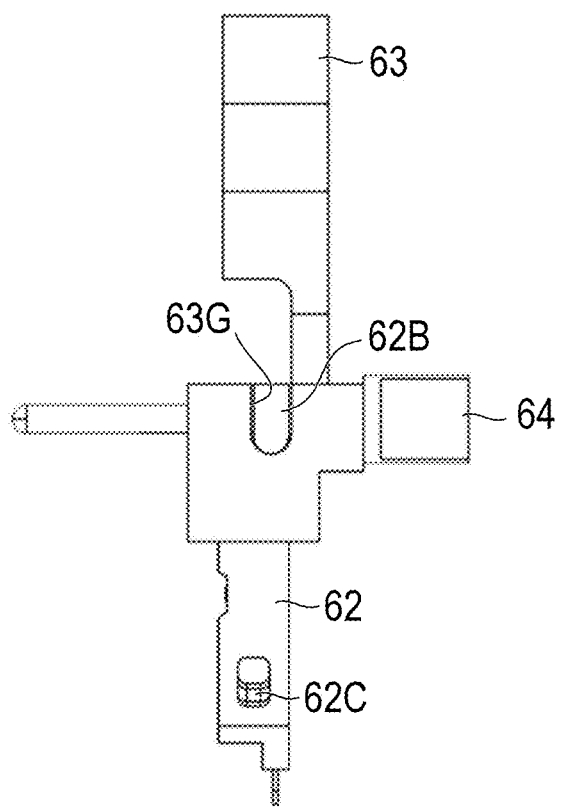

As illustrated in FIGS. 22A and 22B, the first elongated portion 62B of the second gel adaptor holder 62 is placed in the recess 63G. The recess 63G is configured into a recessed shape so as to extend along the circular shape of the lower part of the first elongated portion 62B of the second gel adaptor holder 62.

The pin 64 is passed through the through hole 63H. The through hole 63H is configured so that its diameter is slightly larger than the outer diameter of the pin 64.

Figure 21:
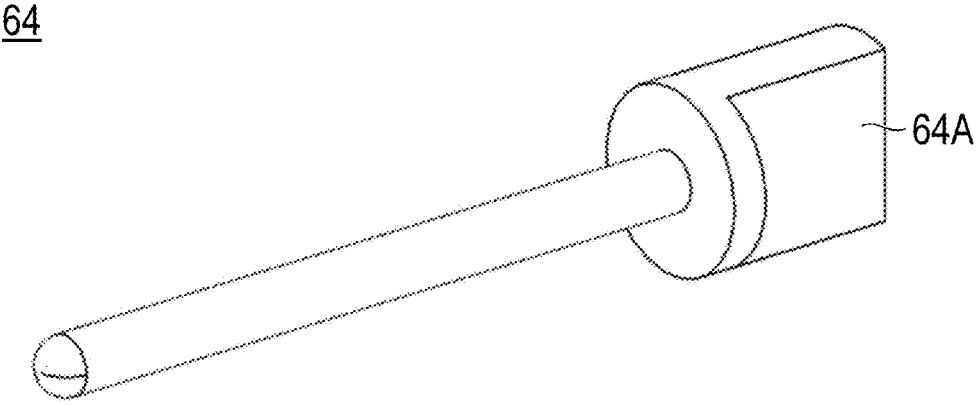
FIG. 21 is a perspective view illustrating a pin of the tension measuring device of the second embodiment.

As illustrated in FIGS. 17, 22A and 22B, the pin 64 is inserted through the through hole 62H of the second gel adaptor holder 62, and the through hole 63H of the rod 63. As illustrated in FIG. 21, a grasping portion 64A that can be grasped is configured in the pin 64. The user inserts the pin 64 through the through hole 63H of the rod 63 and the through hole 62H of the second gel adaptor bolder 62 in this sequence while grasping the grasping portion 64A.

In the state where the first elongated portion 62B of the second gel adaptor holder 62 is placed in the recess 63G of the rod 63 as illustrated in FIGS. 22A and 22B, specifically, the pin 64 is inserted through the through hole 63H of the rod 63 and the through hole 62H of the second gel adaptor holder 62 in this sequence, whereby the second gel adaptor bolder 62 and the rod 63 are connected to each other.

As illustrated in FIG. 17, the first gel adaptor holder 61 is fixed to the culture medium tank 65. The first gel adaptor holder 61, the second gel adaptor holder 62, and the like are accommodated in the culture medium tank 65.

Figure 23A:
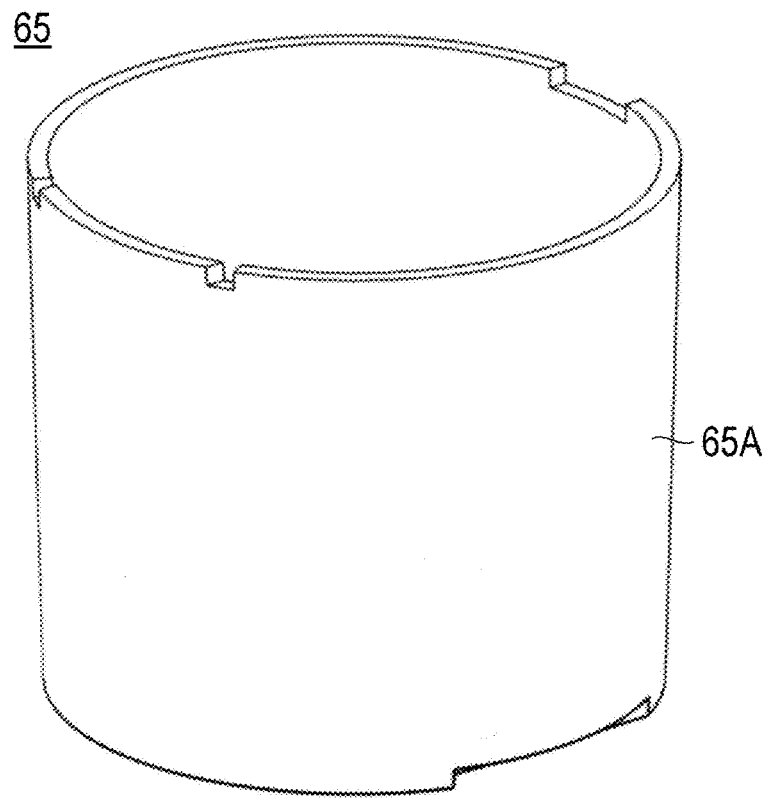
FIGS. 23A and 23B are a perspective view and plan view illustrating a culture medium tank of the tension measuring device of the second embodiment.
Figure 23B:
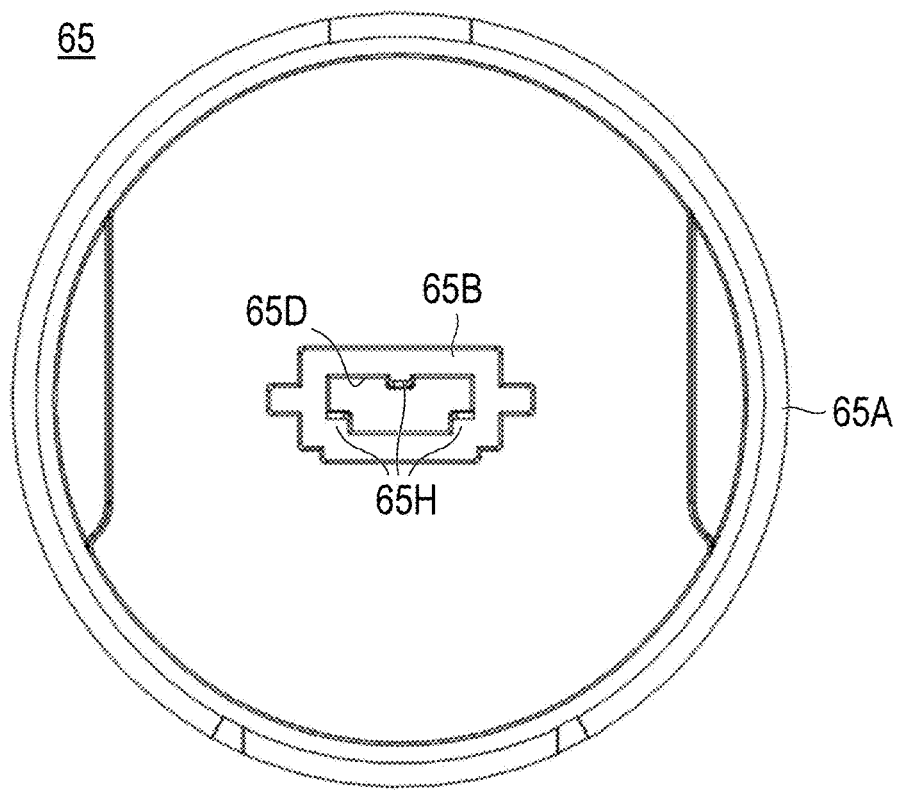

As illustrated in FIGS. 23A and 23B, the culture medium tank 65 may include a culture medium tank body 65A that is configured into a cylindrical shape, and a second fitting portion 65B that is configured so that the first fitting portion 61B of the first gel adaptor holder 61 can be fitted. The culture medium tank body 65A of the culture medium tank 65 in the second embodiment is configured in an approximately same manner as the culture medium tank body 20 of the culture medium tank 2 in the above-described first embodiment, and therefore its description will be omitted.

As illustrated in FIGS. 17 and 23B, the second fitting portion 65B is configured integrally with the culture medium tank body 65A, and so as to be upwardly protruded from the culture medium tank body 65A. As illustrated in FIGS. 17 and 23B, the second fitting portion 65B may include a protruding portion 65C that protrudes upwardly, and an insertion receiving portion 65D that is formed inside the protruding portion 65C.

Three protruding portions 65H that protrude inwardly and opposingly are formed in the insertion receiving portion 65D. When the first fitting portion 61B is inserted into the insertion receiving portion 65D of the thus configured second fitting portion 65B, the first protruding portion 61E of the first fitting portion 61B is elastically deformed in accordance with the shape of the insertion receiving portion 65D. The elastic force due to the elastic deformation causes the first gel adaptor holder 61 to be fixed to the culture medium tank 65.

The configuration of the tension measuring device 6 of the second embodiment has been described above. Next, the configuration of a kit for the tension measuring device 6 that is used together with the tension measuring device 6 will be described. The kit for the tension measuring device 6 may include the connecting members 66, the substrate 67, the gel forming cover 68, the rod holding jig 69, the rear cover 70, and the front cover 71.

In order to form the gel G in the tension measuring device 6, the connecting members 66, the substrate 67, and the gel forming cover 68 are used (see FIGS. 24A to 27). Hereinafter, their configurations will be described.

As illustrated in FIG. 17, the connecting members 66 connect the first gel adaptor holder 61 and the second gel adaptor holder 62 to each other. During the time period when the tension measuring device 6 performs the measurement, the connecting members 66 are detached from the first gel adaptor holder 61 and the second gel adaptor holder 62. As illustrated in FIG. 17, the connecting members 66 are paired in the lateral direction. The connecting members 66 that are paired in the lateral direction are configured so as to be laterally symmetrical about the vertical line.

Figure 24A:
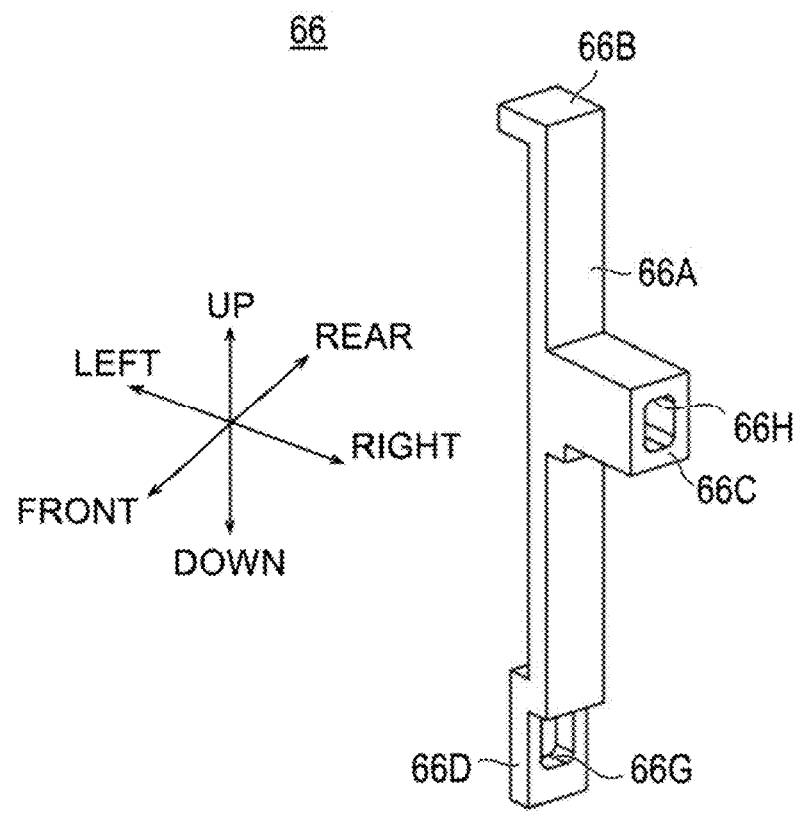
FIGS. 24A and 24B are a perspective view and front view illustrating one of the connecting members that are used together with the tension measuring device of the second embodiment.
Figure 24B:
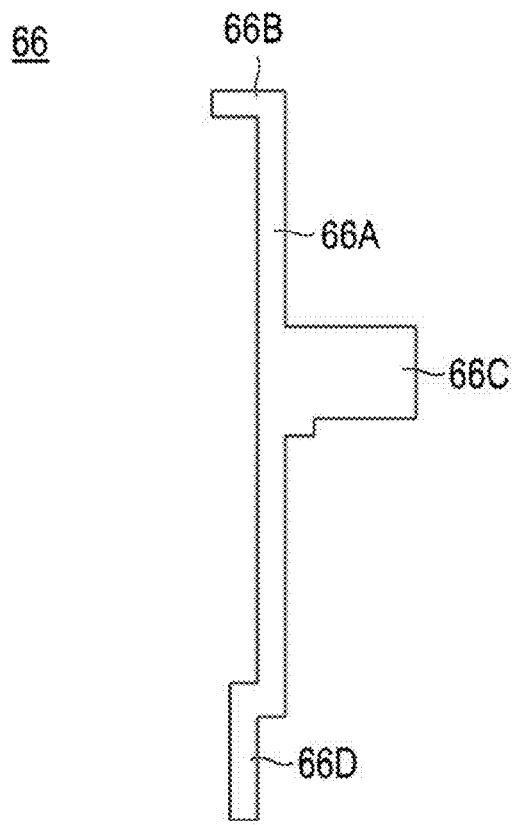
Figure 26:
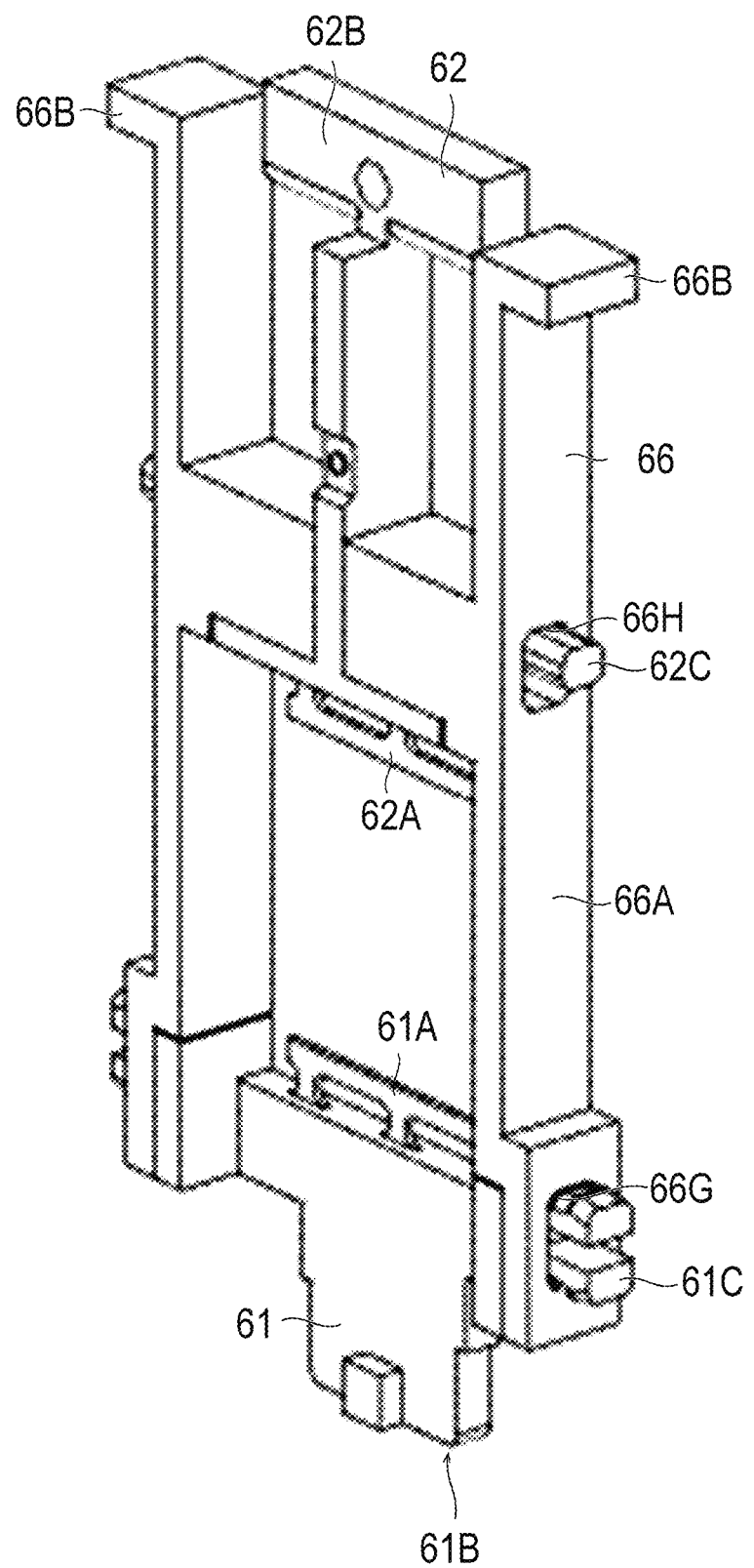
FIG. 26 is a perspective view illustrating a manner in which the first gel adaptor holder and the second gel adaptor holder are connected to each other by the connecting members.

In the pair of connecting members 66, hereinafter, the configuration of the connecting member 66 that is disposed in the left side in FIGS. 17 and 26 will be representatively described. As illustrated in FIGS. 24A and 24B, the connecting member 66 may include a second elongated portion 66A that is elongated in the vertical direction, a third elongated portion 66B that is elongated in the leftward direction from the upper part of the second elongated portion 66A, a fourth elongated portion 66C that is elongated in the rightward direction from the vicinity of the middle in the vertical direction of the second elongated portion 66A, and a fifth elongated portion 66D that is elongated in the downward direction from the lower part of the second elongated portion 66A.

Inside the fourth elongated portion 66C, the first through hole 66H is formed in the lateral direction. As illustrated in FIGS. 17 and 26, the sleeve portion 62C of the second gel adaptor holder 62 is passed through the first through hole 66H.

The second through hole 66G is formed in the lateral direction in the fifth elongated portion 66D. As illustrated in FIGS. 17 and 26, the fixing portion 61C of the first gel adaptor holder 61 is passed through the second through hole 66G, and engaged with the second through hole 66G.

Figure 25A:
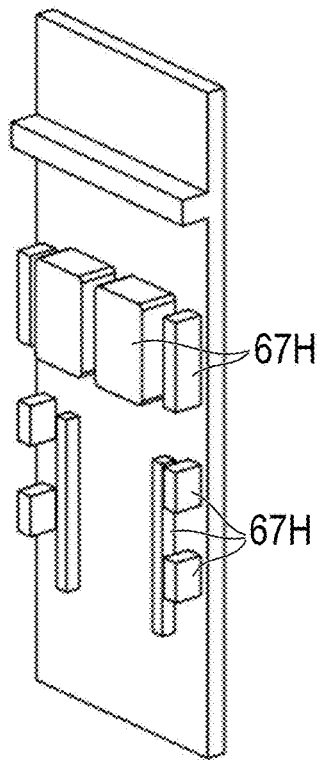
FIGS. 25A and 25B are a perspective view and front view illustrating a substrate that is used together with the tension measuring device of the second embodiment.
Figure 25B:
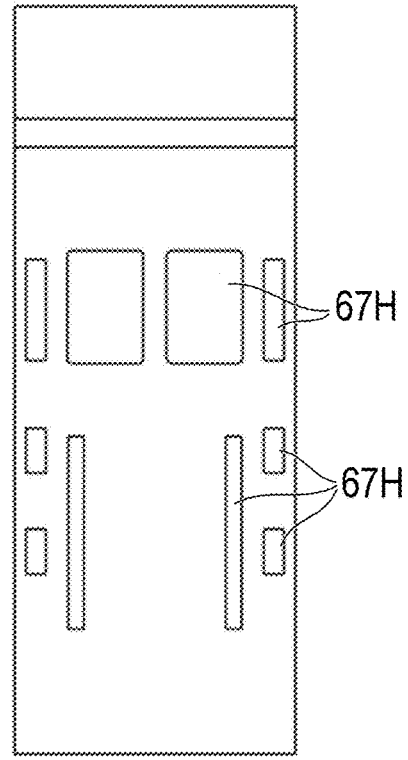
Figure 27:
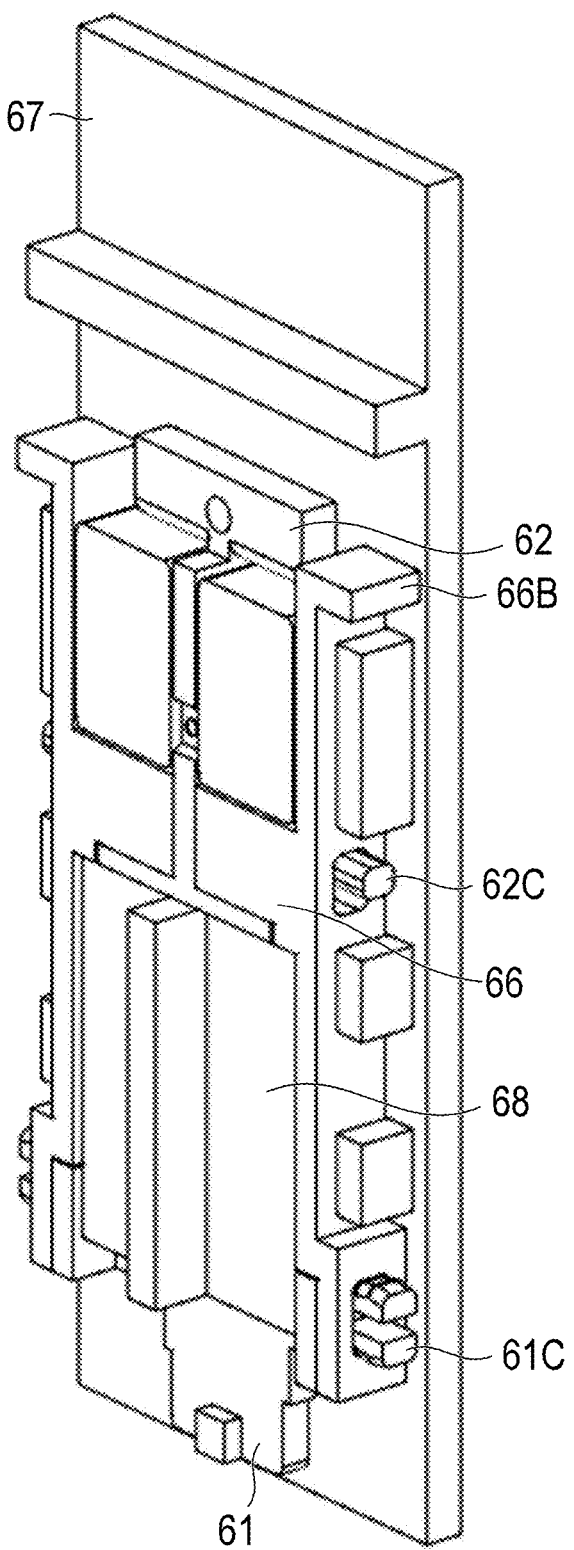
FIG. 27 is a perspective view illustrating a manner in which the first gel adaptor holder and second gel adaptor holder that are connected to each other by the connecting members are placed on the substrate, and a gel forming cover is placed.

As illustrated in FIG. 27, the first gel adaptor holder 61 and second gel adaptor holder 62 that are in the state where they are connected to each other by the connecting members 66 are placed on the substrate 67. As illustrated in FIGS. 25A and 25B, the substrate 67 may include a plurality of convex portions 67H so as to enable the first gel adaptor holder 61 and second gel adaptor holder 62 that are in the state where they are connected to each other by the connecting members 66, to be placed on the substrate. The first gel adaptor holder 61 and second gel adaptor holder 62 that are in the state where they are connected to each other by the connecting members 66 are fitted into a recess formed among the plurality of convex portions 67H. The substrate 67 in the second embodiment has the same function as the substrate 13 in the first embodiment, and therefore a detailed description of the configuration of the substrate will be omitted.

The gel forming cover 68 has the same configuration as the gel forming cover 14 in the above-described first embodiment, and therefore its description will be omitted.

While describing a method of using the kit, hereinafter, also the configurations of the rod holding jig 69, the rear cover 70, and the front cover 71 will be described.

The method of forming the gel, and that of acquiring a cell structure containing muscle cells are same or similar to those in the first embodiment, and therefore their description will be omitted. During the formation of the gel, as illustrated in FIG. 27, the first gel adaptor holder 61 and the second gel adaptor holder 62 are connected to each other by the connecting members 66.

Figure 28A:
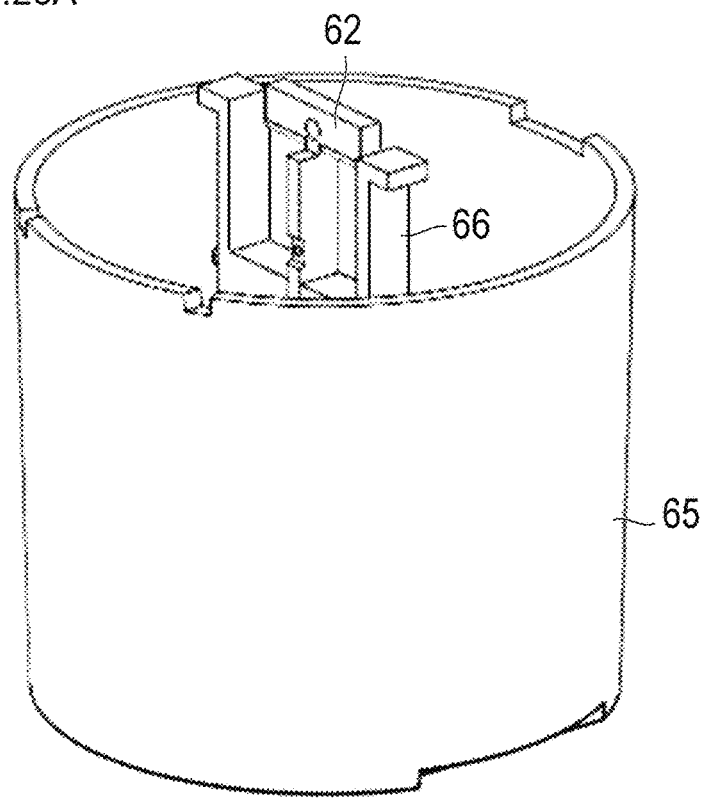
FIGS. 28A and 28B are a perspective view and section view illustrating a manner in which the first gel adaptor holder and second gel adaptor holder that are connected to each other by the connecting members are fixed to the culture medium tank.
Figure 28B:
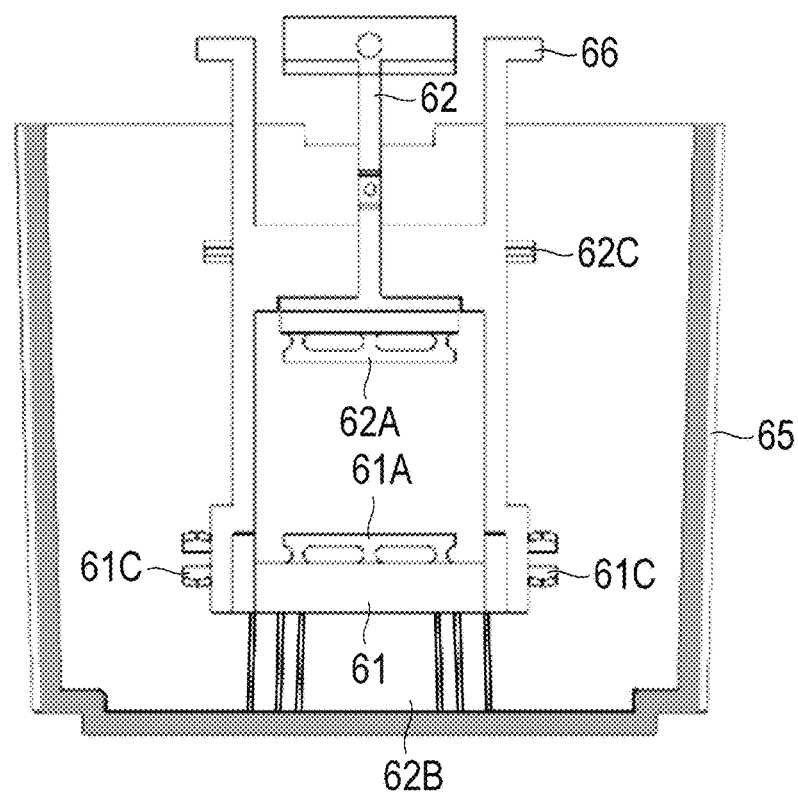

In the state where the first gel adaptor holder 61 and the second gel adaptor holder 62 are connected to each other by the connecting members 66, then, the first gel adaptor holder 61 and the second gel adaptor holder 62 are lifted in the vertical direction, and the first fitting portion 61B of the first gel adaptor holder 61 is fixed to the second fitting portion 65B of the culture medium tank 65 as illustrated in FIGS. 28A and 28B. At this time, since the first gel adaptor holder 61 and the second gel adaptor holder 62 are connected to each other by the connecting members 66, the gel G which is placed between the first gel adaptor holder 61 and the second gel adaptor holder 62, and to which the cell structure CS is bonded can be preferably prevented from application of a pulling force, and therefore the cell structure CS can be preferably prevented from being damaged.

As illustrated in FIG. 29, next, the rod holding jig 69 is fixed to the culture medium tank 65, and the rod 63 is held by the rod holding jig 69. Hereinafter, the configuration of the rod holding jig 69 will be described.

As illustrated in FIG. 29, the rod holding jig 69 may include a planar portion 69A that is planarly configured, and a vertical wall portion 69B that is raised from the planar portion 69A. A pair of recesses 69C in which projections 70B of the rear cover 70 that will be described later are to be placed respectively are formed in the planar portion 69A. The rod holding portion 69D that can hold the constricted part 63E of the rod 63 is formed in the rear of the vertical wall portion 69B. When the rod 63 is inserted toward the constricted part 63E until the rod is contacted with the upper surface of the rod holding portion 69D, the rod holding portion 69D supports the rod 63, and grasps the constricted part 63E.

Figure 30:
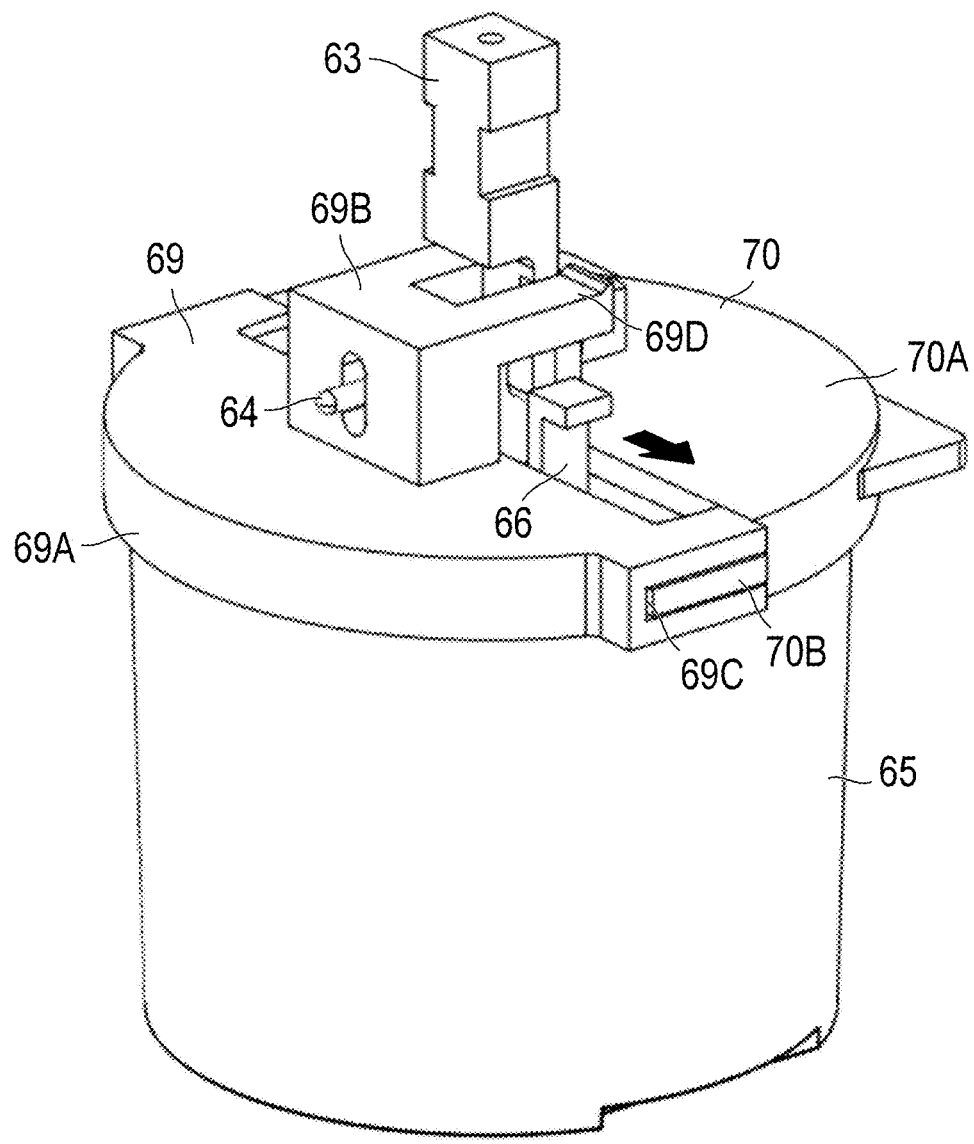
FIG. 30 is a perspective view illustrating a manner in which, in the state illustrated in FIG. 29, a rear cover is attached to the culture medium tank.

As illustrated in FIG. 30, next, the rear cover 70 is fixed to the culture medium tank 65, and the projections 70B of the rear cover 70 are inserted into the recesses 69C of the rod holding jig 69, respectively. As illustrated in FIG. 30, the rear cover 70 may include a planar portion 70A that is planarly configured, and protruding portions 70B that are disposed in end parts of the planar portion 70A, respectively.

Figure 31A:
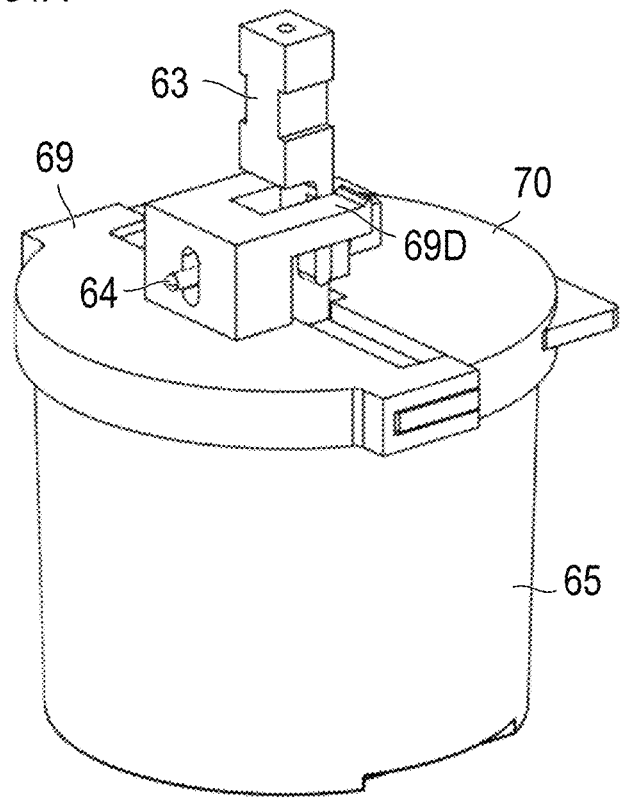
FIGS. 31A and 31B are a perspective view and section view illustrating a manner in which the connecting members are removed from the state illustrated in FIG. 30.
Figure 31B:
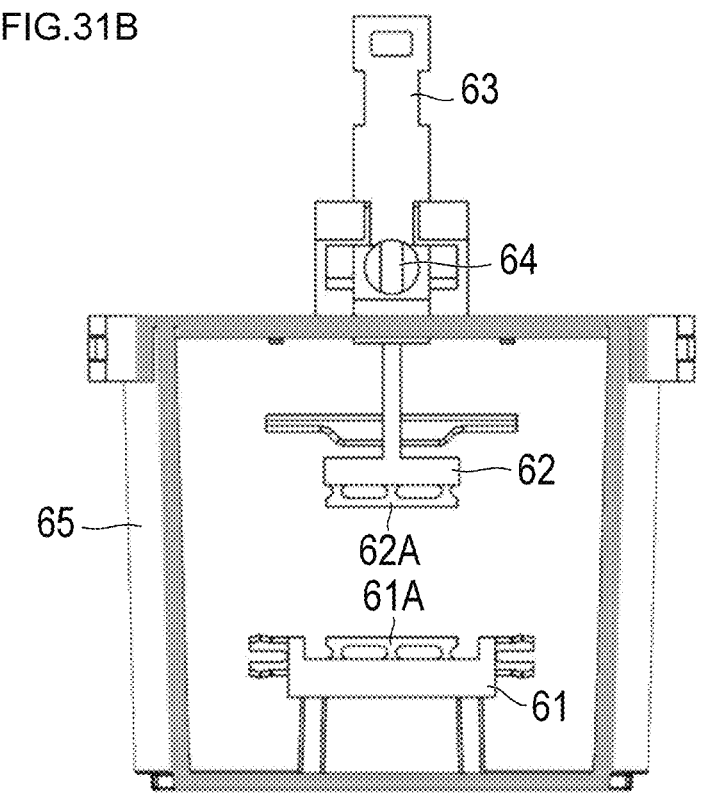

As illustrated in FIGS. 31A and 31B, then, the third elongated portions 66B of the connecting members 66 that are upward protruded from a gap between the rod holding jig 69 and the rear cover 70 are outward slid in the lateral directions (see the arrow in FIG. 30), thereby detaching the connecting members 66 from the first gel adaptor holder 61 and the second gel adaptor holder 62. At this time, since the rod 63 is held by the rod holding portion 69D of the rod holding jig 69, the positions of the rod 63, the gel G to which the cell structure CS is bonded, and the like can be maintained even when the connecting members 66 are detached.

Figure 32:
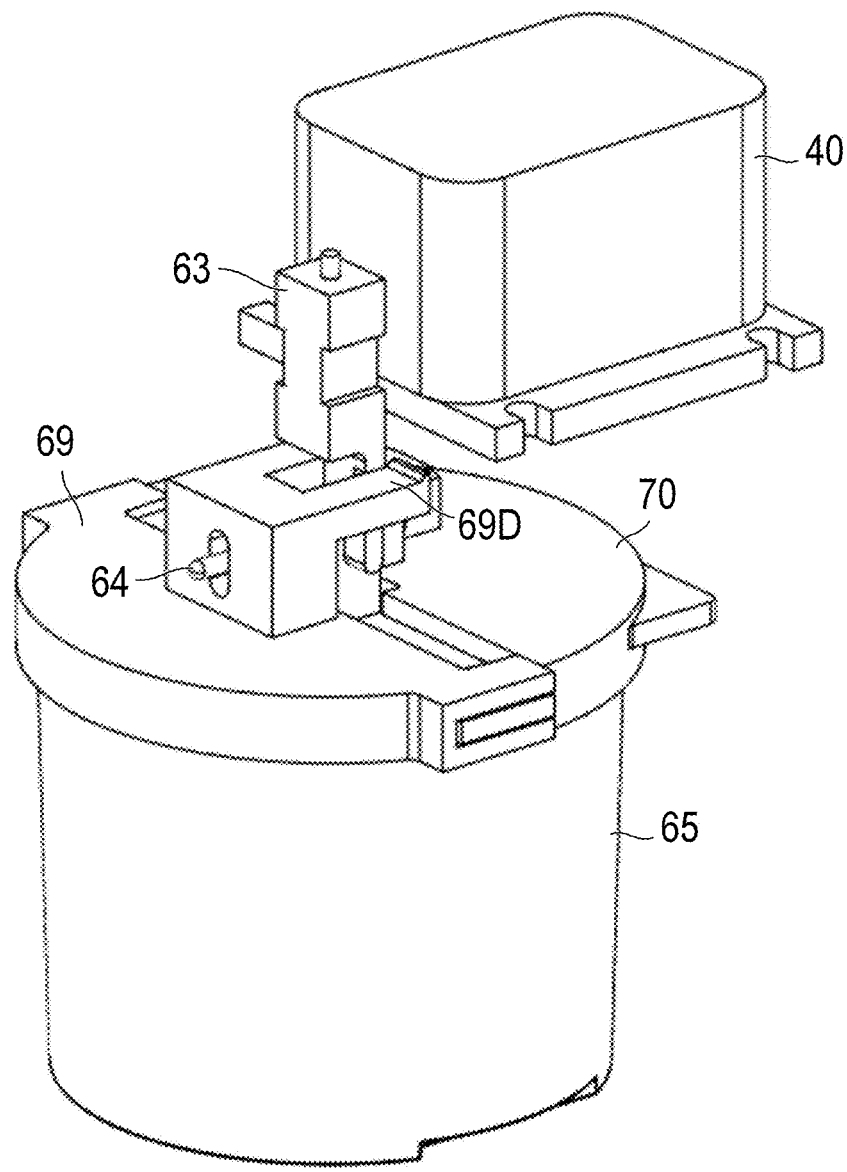
FIG. 32 is a perspective view illustrating a manner in which, in the state illustrated in FIG. 31A, the rod is connected to a tension detecting unit.
Figure 33:
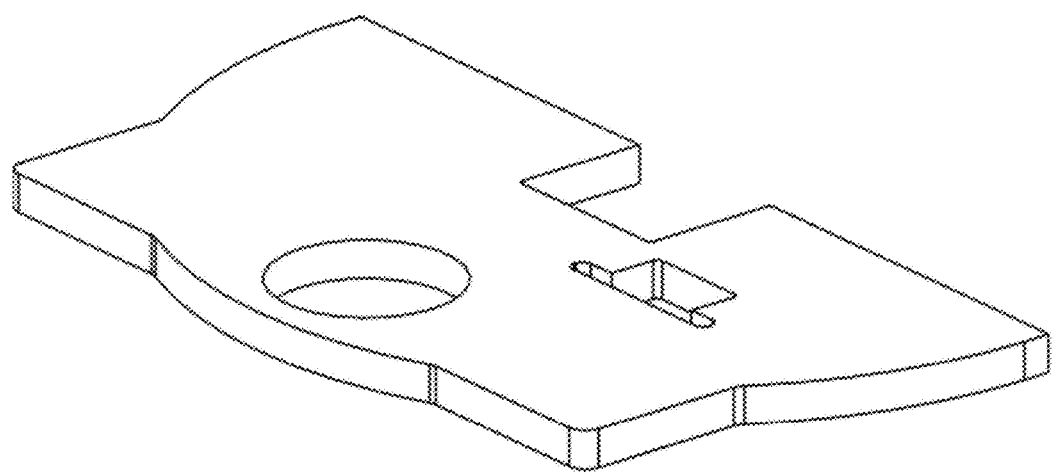
FIG. 33 is a perspective view illustrating a front cover.

As illustrated in FIG. 32, then, the rod 63 is connected to the tension detecting unit 40. At this time, even in a state where the connecting members 66 are detached, the rod 63 is held to a predetermined position by the rod holding jig 69, and therefore the connection can be easily performed by sliding the culture medium tank 65. After the rod 63 is connected to the tension detecting unit 40, the rod holding jig 69 is detached, and the front cover 71 illustrated in FIG. 33 is fixed to the same position as that to which the rod holding jig 69 was attached.

As described above, the tension measuring device 6 of the second embodiment is a device for measuring the tension of a cell structure containing muscle cells. The tension measuring device 6 has: the first gel adaptor holder 61 including the first gel holding portion 61A for fixing the one end of the gel G, and the first fitting portion 61B; the second gel adaptor holder 62 including the second gel holding portion 62A that fixes the other end of the gel G, and that is disposed to be opposed to the first gel holding portion 61A; the culture medium tank 65 in which the first gel adaptor holder 61 and the second gel adaptor holder 62 are accommodated, and which includes the second fitting portion 65B that is configured to be able to be fitted to the first fitting portion 611B; and the fixing portions 61C to which the connecting members 66 for connecting the first gel adaptor holder 61 and the second gel adaptor holder 62 to each other are able to be fixed. According to the thus configured tension measuring device 6, it is possible to easily measure the tension of a cell structure containing muscle cells.

Moreover, the fixing portions 61C are disposed in the first gel adaptor holder 61, and able to be engaged with the connecting members 66. According to the configuration, the connecting members 66 can be surely fixed to the first gel adaptor bolder 61 and the second gel adaptor holder 62.

Moreover, the tension measuring device 6 further has the rod 63 that connects the tension detecting unit 40 and the second gel adaptor holder 62 to each other. The second gel adaptor holder 62 further has the first elongated portion 62B that is disposed above the second gel holding portion 62A, and the rod 63 has the recess 63G into which the first elongated portion 62B is to be inserted. The second gel adaptor holder 62 and the rod 63 are connected to each other by, in the state where the first elongated portion 62B is inserted into the recess 63G, inserting the pin 64 into the first elongated portion 62B and the recess 63G. According to the configuration, the rod 63 and the second gel adaptor holder 62 are surface-contacted with each other, they are fixed to each other by the pin 64, and therefore the rod 63 and the second gel adaptor holder 62 can be appropriately restrained.

Moreover, the second gel adaptor holder 62 has the pair of sleeve portions 62C that are slidably inserted into the connecting members 66, respectively. According to the configuration, in the case where the connecting members 66 are to be detached from the first gel adaptor holder 61 and the second gel adaptor holder 62, the connecting members can be easily detached.

The kit of the second embodiment and for the tension measuring device 6 has: the first gel adaptor holder 61 including the first gel holding portion 61A for fixing the one end of the gel G, and the first fitting portion 61B; the second gel adaptor holder 62 including the second gel holding portion 62A that fixes the other end of the gel G, and that is disposed to be opposed to the first gel holding portion 61A; the culture medium tank 65 in which the first gel adaptor holder 61 and the second gel adaptor holder 62 are accommodated, and which includes the second fitting portion 65B that is configured to be able to be fitted to the first fitting portion 61B; the connecting members 66 for connecting the first gel adaptor holder 61 and the second gel adaptor holder 62 to each other; the substrate 67 into which the first gel adaptor holder 61 land second gel adaptor holder 62 that are connected to each other are to be fitted; and the fixing portions 61C to which the connecting members 66 are able to be fixed. According to the thus configured kit, when the first fitting portion 61B of the first gel adaptor holder 61 is to be fixed to the second fitting portion 65B of the culture medium tank 65 by lifting the first gel adaptor holder 61 and the second gel adaptor holder 62 in the vertical direction, the gel G to which the cell structure CS is bonded can be preferably prevented from application of a pulling force, and therefore the cell structure CS can be preferably prevented from being damaged.

Moreover, the kit has: the rod 63 that connects the tension detecting unit 40 and the second gel adaptor holder 62 to each other; and the rod holding jig 69 that is able to be fixed to the top portion of the culture medium tank 65, and that includes the rod holding portion 69D which is able to hold the rod 63. According to the thus configured kit, even when the connecting members 66 are detached, the positions of the rod 63, the gel G to which the cell structure CS is bonded, and the like can be maintained.

The presently disclosed subject matter is not limited to the above-described embodiments, but can be variously modified within the scope of the appended claims.

In the above-described second embodiment, for example, the fixing portions 61C are disposed in the first gel adaptor holder 61. As far as the connecting members 66 are fixed to the fixing portions 61C, however, the fixing portions are disposed in arbitrary positions, and their shapes are not limited. Moreover, the wide parts 61H that are disposed in the pair of elastically deformable elastic members 61G of the fixing portions 61C may be disposed in at least one of the upper and lower sides of the elastic members 61G.

In the above-described second embodiment, moreover, the second gel adaptor holder 62 and the rod 63 are fixed to each other by the pin 64 in the state where the first elongated portion 62B of the second gel adaptor holder 62 is inserted into the recess 63G of the rod 63, whereby they are connected to each other. However, the means for connecting the second gel adaptor holder 62 and the rod 63 to each other is not limited to the above-described configuration.

In the above-described second embodiment, moreover, the first gel adaptor holder includes the first fitting portion 61B, and the first fitting portion 61B is inserted into the insertion receiving portion 65D of the second fitting portion 65B, whereby the first gel adaptor holder 61 is fixed to the culture medium tank 65 while the first protruding portion 61E of the first fitting portion 61B coincides with the shape of the insertion receiving portion 65D. However, the presently disclosed subject matter is not limited to the configuration as far as the first gel adaptor holder and the second gel adaptor holder can be fixed. For example, a configuration may be employed in which the first fitting portion 61B of the first gel adaptor holder, and the insertion receiving portion 65D of the second fitting portion 65B may be exchanged with each other, and they may be placed in arbitrary positions. Furthermore, their shapes are not limited to the above-described shapes.

What is claimed is:

1. A device for measuring a tension of a cell structure containing muscle cells comprising:
    a first gel adaptor holder that includes: a frame member; and a first gel holding portion that, for fixing one end of a gel, is disposed protrudingly from a part of a side inner surface of the frame member, the frame member including: a cutaway in an upper portion of the frame member at a position opposed to the first gel holding portion; and a pair of first grasping portions that are formed by the cutaway, an upper portion of the frame member having a pair of claw portions; and
    a second gel adaptor holder that includes: a second gel holding portion for fixing another end of the gel; and a connecting portion that is connected to the second gel holding portion through a coupling portion,
    wherein the second gel adaptor holder is attached to the first gel adaptor holder by causing the first grasping portions to grasp the connecting portion so that, inside the frame member, the second gel holding portion is opposed to the first gel holding portion, and
    wherein a gap between the pair of first grasping portions is increased when the pair of claw portions are fitted to a cover of a culture medium tank.

2. The device according to claim 1, further comprising a gel disposed between the first gel holding portion and the second gel holding portion.

3. The device according to claim 2, further comprising a cell structure containing muscle cells bonded to the gel.

4. The device according to claim 3, wherein the cell structure is a cell sheet.

5. A system for measuring a tension of a cell structure containing muscle cells comprising:
    the device according to claim 4;
    a body of the culture medium tank in which the device is to be immersed;
    a culture medium tank cover that includes fitting portions which are to be fitted to the pair of claw portions, and a connecting portion through port through which the connecting portion of the second gel adaptor holder is to be passed, and that covers the culture medium tank body;
    a tension detecting unit connected to the connecting portion of the second gel adaptor holder;
    a calculator connected to the tension detecting unit, and applies a calculation to a signal detected by the tension detecting unit to calculate a tension; and
    an outputting unit displays a result of the calculation performed by the calculator.

6. A kit for producing the device according to claim 1 comprising:
    a first gel adaptor holder that includes: a frame member; and a first gel holding portion that, for fixing one end of a gel, is disposed protrudingly from a part of a side inner surface of the frame member, the frame member including: a cutaway in an upper portion of the frame member at a position opposed to the first gel holding portion; and a pair of first grasping portions that are formed by the cutaway, the upper portion of the frame member having a pair of claw portions;
    a second gel adaptor holder that includes: a second gel holding portion for fixing another end of the gel; and a connecting portion that is connected to the second gel holding portion through a coupling portion;
    a substrate that includes a pair of gel shaping convex parts which are fitted along the side inner surface of the frame member; and
    a gel forming cover that includes a surface which is parallel to a gel contacting surface of the substrate, in order to form an upper surface of the gel,
    wherein the second gel adaptor holder is attached to the first gel adaptor holder by causing the first grasping portions to grasp the connecting portion so that, inside the frame member, the second gel holding portion is opposed to the first gel holding portion, and wherein a gap between the pair of first grasping portions is increased when the pair of claw portions are fitted to the culture medium tank cover.

7. A tension measuring device for measuring a tension of a cell structure containing muscle cells, the tension measuring device comprising:
a first gel adaptor holder including a first gel holding portion for fixing one end of a gel;
a second gel adaptor holder including a second gel holding portion that fixes another end of the gel, and that is disposed to be opposed to the first gel holding portion; and
a fixing portion to which connecting members for connecting the first gel adaptor holder and the second gel adaptor holder to each other are able to be fixed,
wherein the fixing portion is disposed in the first gel adaptor holder, and able to be engaged with the connecting members.

8. The tension measuring device according to claim , further including a culture medium tank in which the tension measuring device is accommodated,
wherein the fixing portion is configured to be able to fix the first gel adaptor holder, the second gel adaptor holder and the culture medium tank at an inside of the culture medium tank.

9. The tension measuring device according to claim 7, further including a culture medium tank in which the tension measuring device is accommodated,
wherein the fixing portion is configured to be able to fix the first gel adaptor holder, the second gel adaptor holder and the culture medium tank at a bottom of the culture medium tank.

10. The tension measuring device according to claim 7, wherein the second gel adaptor holder includes a pair of sleeve portions that are slidably inserted into the connecting members, respectively.

11. The tension measuring device according to claim 10, wherein the first gel adaptor holder includes a first fitting portion, and
wherein the tension measuring device further includes a culture medium tank in which the first gel adaptor holder and the second gel adaptor holder are accommodated, and which includes a second fitting portion that is configured to be able to be fitted to the first fitting portion.

12. The tension measuring device according to claim 7 further comprising a rod that connects a tension detecting unit and the second gel adaptor holder to each other,
wherein the second gel adaptor holder further includes a first elongated portion that is disposed above the second gel holding portion,
wherein the rod includes a recess portion into which the first elongated portion is to be inserted, and
wherein the second gel adaptor holder and the rod are connected to each other by, in a state where the first elongated portion is inserted into the recess portion, inserting a fixing member into the first elongated portion and the recess portion.

13. A kit for a tension measuring device for measuring a tension of a cell structure containing muscle cells, the kit comprising:
a first gel adaptor holder including a first gel holding portion for fixing one end of a gel;
a second gel adaptor holder including a second gel holding portion that fixes another end of the gel, and that is disposed to be opposed to the first gel holding portion;
connecting members for connecting the first gel adaptor holder and the second gel adaptor holder to each other;
a substrate into which the first gel adaptor holder and the second gel adaptor holder that are connected to each other by the connecting members are to be fitted; and
a fixing portion to which the connecting members are able to be fixed,
wherein the fixing portion is disposed in the first gel adaptor holder, and able to be engaged with the connecting members.

14. The kit according to claim 13, wherein the first gel adaptor holder includes a first fitting portion, and
wherein the kit further includes a culture medium tank in which the first gel adaptor holder and the second gel adaptor holder are accommodated, and which includes a second fitting portion that is configured to be able to be fitted to the first fitting portion.

15. The kit according to claim 14, further comprising:
a rod that connects a tension detecting unit and the second gel adaptor holder to each other; and
a rod holding jig that is able to be fixed to a top portion of the culture medium tank, and that includes a rod grasping portion which is able to grasp the rod.

16. The kit according to claim 13, wherein the second gel adaptor holder includes a pair of sleeve portions that are slidably inserted into the connecting members, respectively.

17. The kit according to claim 13, further including a culture medium tank in which the tension measuring device is accommodated,
wherein the fixing portion is configured to be able to fix the first gel adaptor holder, the second gel adaptor holder and the culture medium tank at an inside of the culture medium tank.

18. The kit according to claim 13, further including a culture medium tank in which the tension measuring device is accommodated,
wherein the fixing portion is configured to be able to fix the first gel adaptor holder, the second gel adaptor holder and the culture medium tank at a bottom of the culture medium tank.

* * * * *